United States Patent
Quill et al.

(10) Patent No.: US 9,925,044 B2
(45) Date of Patent: Mar. 27, 2018

(54) TRANSCATHETER VALVE WITH TORSION SPRING FIXATION AND RELATED SYSTEMS AND METHODS

(71) Applicant: Medtronic, Inc., Minneapolis, MN (US)

(72) Inventors: Jason Quill, Forest Lake, MN (US); Cynthia T. Clague, Minnetonka, MN (US); Paul T. Rothstein, Elk River, MN (US)

(73) Assignee: Medtronic, Inc., Minneapolis, MN (US)

(*) Notice: Subject to any disclaimer, the term of this patent is extended or adjusted under 35 U.S.C. 154(b) by 196 days.

(21) Appl. No.: 14/156,076

(22) Filed: Jan. 15, 2014

(65) Prior Publication Data
US 2014/0180401 A1 Jun. 26, 2014

Related U.S. Application Data

(63) Continuation of application No. 12/846,962, filed on Jul. 30, 2010, now Pat. No. 8,652,204.
(Continued)

(51) Int. Cl.
*A61F 2/24* (2006.01)
(52) U.S. Cl.
CPC .......... *A61F 2/2403* (2013.01); *A61F 2/2418* (2013.01); *A61F 2/2436* (2013.01);
(Continued)
(58) Field of Classification Search
CPC .... A61F 2/848; A61F 2/86; A61F 2/88; A61F 2/95; A61F 2/2403; A61F 2/2418; A61F 2/2436; A61F 2220/0008; A61F 2220/0013; A61F 2220/0016; A61F 2/243; A61F 2/2439
See application file for complete search history.

(56) References Cited

U.S. PATENT DOCUMENTS 3,334,629 A  8/1967  Cohn
3,409,013 A  11/1968 Berry
(Continued)

FOREIGN PATENT DOCUMENTS

CN    101011298 A   8/2007
DE    3640745 C2    3/1992
(Continued)

OTHER PUBLICATIONS

Andersen, H. et al., "Transluminal implantation of artificial heart valves. Description of a new expandable aortic valve and initial results with implantation by catheter technique in closed chest pigs." *Euro. Heart J.* 13:704-708 (1992).
(Continued)

*Primary Examiner* — Sarah W Aleman
(74) *Attorney, Agent, or Firm* — Medler Ferro Woodhouse & Mills

(57) ABSTRACT

Described is a prosthetic valve, comprising: an expandable stent including an inner lumen and having a first and a second end; and a spring attached to the first end of the expandable stent; wherein the expandable stent and the spring can expand radially to a desired diametric configuration in order to anchor the prosthetic valve at an implantation position in a body lumen. Related systems and methods.

22 Claims, 14 Drawing Sheets

Related U.S. Application Data

(60) Provisional application No. 61/320,111, filed on Apr. 1, 2010.

(52) U.S. Cl.
CPC .......... A61F 2220/0008 (2013.01); A61F 2220/0016 (2013.01); A61F 2230/0013 (2013.01)

(56) References Cited

U.S. PATENT DOCUMENTS

| | | |
|---|---|---|
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,078,268 A | 3/1978 | Possis |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,491,986 A | 1/1985 | Gabbay |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,834,755 A | 5/1989 | Silvestrini et al. |
| 4,846,830 A | 7/1989 | Knoch et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,104,399 A | 4/1992 | Lazarus |
| 5,108,425 A | 4/1992 | Hwang |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,178,632 A | 1/1993 | Hanson |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum |
| 5,344,442 A | 9/1994 | Deac |
| 5,350,398 A | 9/1994 | Pavcnik et al. |
| 5,354,330 A | 10/1994 | Hanson et al. |
| 5,370,685 A | 12/1994 | Stevens |
| 5,389,106 A | 2/1995 | Tower |
| 5,397,351 A | 3/1995 | Pavcnik et al. |
| 5,397,355 A | 3/1995 | Marin et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,720,776 A | 2/1998 | Chuter et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |

(56) References Cited

U.S. PATENT DOCUMENTS

| | | | |
|---|---|---|---|
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,908,451 A | 6/1999 | Yeo |
| 5,908,452 A | 6/1999 | Bokros et al. |
| 5,913,842 A | 6/1999 | Boyd et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,964,405 A | 10/1999 | Benary et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV et al. |
| 6,051,014 A | 4/2000 | Jang |
| 6,059,809 A | 5/2000 | Amor et al. |
| 6,076,742 A | 6/2000 | Benary |
| 6,091,042 A | 7/2000 | Benary |
| 6,102,944 A | 8/2000 | Huynh et al. |
| 6,110,201 A | 8/2000 | Quijano et al. |
| 6,113,612 A | 9/2000 | Swanson et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevillon et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,287,339 B1 | 9/2001 | Vazquez et al. |
| 6,296,662 B1 | 10/2001 | Caffey |
| 6,299,637 B1 | 10/2001 | Shaolian et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,312,465 B1 | 11/2001 | Griffin et al. |
| 6,327,772 B1 | 12/2001 | Zadno-Azizi et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,558,418 B2 | 5/2003 | Carpentier et al. |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,572,652 B2 * | 6/2003 | Shaknovich ............ A61F 2/24 623/1.24 |
| 6,582,462 B1 | 6/2003 | Andersen et al. |
| 6,585,758 B1 | 7/2003 | Chouinard et al. |
| 6,592,546 B1 | 7/2003 | Barbut et al. |
| 6,600,803 B2 | 7/2003 | Bruder |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,632,243 B1 | 10/2003 | Zadno-Azizi et al. |
| 6,635,068 B1 | 10/2003 | Dubrul et al. |
| 6,635,085 B1 | 10/2003 | Caffey et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,121 B2 | 5/2004 | Ortiz et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,767,362 B2 | 7/2004 | Schreck |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence et al. |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof et al. |
| 6,846,325 B2 | 1/2005 | Liddicoat |
| 6,866,650 B2 | 3/2005 | Stevens et al. |
| 6,872,223 B2 | 3/2005 | Roberts et al. |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Strecter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin, Jr. et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |

(56) References Cited

U.S. PATENT DOCUMENTS

| | | |
|---|---|---|
| 7,018,406 B2 | 3/2006 | Seguin et al. |
| 7,018,408 B2 | 3/2006 | Bailey et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,128,759 B2 | 10/2006 | Osborne et al. |
| 7,137,184 B2 | 11/2006 | Schreck |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,261,732 B2 | 8/2007 | Justino |
| 7,267,686 B2 | 9/2007 | DiMatteo et al. |
| 7,300,457 B2 | 11/2007 | Palmaz |
| 7,300,463 B2 | 11/2007 | Liddicoat |
| 7,311,730 B2 | 12/2007 | Gabbay |
| 7,316,706 B2 | 1/2008 | Bloom et al. |
| 7,329,278 B2 | 2/2008 | Seguin et al. |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Schreck |
| 7,384,411 B1 | 6/2008 | Condado |
| 7,399,315 B2 | 7/2008 | Iobbi |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,284 B2 | 12/2008 | Lambrecht et al. |
| 7,470,285 B2 | 12/2008 | Nugent et al. |
| 7,481,838 B2 | 1/2009 | Carpentier et al. |
| 7,491,228 B2 | 2/2009 | Doran et al. |
| 7,524,331 B2 | 4/2009 | Birdsall |
| 7,544,206 B2 | 6/2009 | Cohn |
| 7,547,322 B2 | 6/2009 | Sarac et al. |
| 7,556,386 B2 | 7/2009 | Smith |
| 7,556,646 B2 | 7/2009 | Yang et al. |
| 7,585,321 B2 | 9/2009 | Cribier |
| 7,611,534 B2 | 11/2009 | Kapadia et al. |
| 7,611,535 B2 | 11/2009 | Woolfson et al. |
| 7,618,446 B2 | 11/2009 | Andersen et al. |
| 7,621,948 B2 | 11/2009 | Hermann et al. |
| 7,625,403 B2 | 12/2009 | Krivoruchko |
| 7,635,386 B1 | 12/2009 | Gammie |
| 7,637,946 B2 | 12/2009 | Solem et al. |
| 7,682,390 B2 | 3/2010 | Seguin |
| 7,748,389 B2 | 7/2010 | Salahieh et al. |
| 7,780,726 B2 | 8/2010 | Seguin |
| 7,806,919 B2 | 10/2010 | Bloom et al. |
| 7,959,672 B2 | 6/2011 | Salahieh et al. |
| 8,449,599 B2 * | 5/2013 | Chau .................... A61F 2/2418 623/1.24 |
| 9,060,892 B2 * | 6/2015 | Oepen et al. |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0026233 A1 | 2/2002 | Shaknovich |
| 2002/0029014 A1 | 3/2002 | Jayaraman |
| 2002/0032480 A1 | 3/2002 | Spence et al. |
| 2002/0032481 A1 * | 3/2002 | Gabbay .................... 623/2.11 |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0077696 A1 | 6/2002 | Zadno-Azizi et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0186558 A1 | 12/2002 | Plank et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130727 A1 | 7/2003 | Drasler et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0158595 A1 | 8/2003 | Randall et al. |
| 2003/0171805 A1 | 9/2003 | Berg et al. |
| 2003/0181850 A1 | 9/2003 | Diamond et al. |
| 2003/0191519 A1 | 10/2003 | Lombardi et al. |
| 2003/0195609 A1 * | 10/2003 | Berenstein ............. A61F 2/856 623/1.15 |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0209835 A1 | 11/2003 | Chun et al. |
| 2003/0212410 A1 | 11/2003 | Stenzel et al. |
| 2003/0212452 A1 | 11/2003 | Zadno-Azizi et al. |
| 2003/0212454 A1 | 11/2003 | Scott et al. |
| 2003/0225445 A1 | 12/2003 | Derus et al. |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0044402 A1 | 3/2004 | Jung et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0059429 A1 | 3/2004 | Amin et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093070 A1 | 5/2004 | Hojeibane et al. |
| 2004/0093075 A1 | 5/2004 | Kuehne |
| 2004/0097788 A1 | 5/2004 | Mourlas et al. |

(56) References Cited

U.S. PATENT DOCUMENTS

| | | |
|---|---|---|
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty et al. |
| 2004/0127979 A1 | 7/2004 | Wilson et al. |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson, IV et al. |
| 2004/0167620 A1 | 8/2004 | Ortiz et al. |
| 2004/0186563 A1 | 9/2004 | Lobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran et al. |
| 2004/0215339 A1 | 10/2004 | Drasler et al. |
| 2004/0225353 A1 | 11/2004 | McGuckin, Jr. et al. |
| 2004/0225354 A1 | 11/2004 | Allen et al. |
| 2004/0236411 A1 | 11/2004 | Sarac et al. |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060029 A1 | 3/2005 | Le et al. |
| 2005/0060030 A1 | 3/2005 | Lashinski et al. |
| 2005/0075584 A1 | 4/2005 | Cali |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075725 A1 | 4/2005 | Rowe |
| 2005/0075727 A1 | 4/2005 | Wheatley |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua et al. |
| 2005/0119688 A1 | 6/2005 | Bergheim |
| 2005/0131438 A1 | 6/2005 | Cohn |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137695 A1 | 6/2005 | Salahieh et al. |
| 2005/0137698 A1 | 6/2005 | Salahieh et al. |
| 2005/0137701 A1 | 6/2005 | Salahieh et al. |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0171597 A1* | 8/2005 | Boatman .................. A61F 2/07 623/1.22 |
| 2005/0182483 A1 | 8/2005 | Osborne et al. |
| 2005/0187616 A1 | 8/2005 | Realyvasquez |
| 2005/0192527 A1 | 9/2005 | Gharib et al. |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy et al. |
| 2005/0222674 A1 | 10/2005 | Paine |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin, Jr. et al. |
| 2006/0025855 A1 | 2/2006 | Lashinski et al. |
| 2006/0025857 A1 | 2/2006 | Bergheim et al. |
| 2006/0047338 A1 | 3/2006 | Jenson et al. |
| 2006/0052867 A1 | 3/2006 | Revuelta et al. |
| 2006/0058775 A1 | 3/2006 | Stevens et al. |
| 2006/0058872 A1 | 3/2006 | Salahieh et al. |
| 2006/0074484 A1 | 4/2006 | Huber |
| 2006/0074485 A1 | 4/2006 | Realyvasquez |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0149360 A1 | 7/2006 | Schwammenthal et al. |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoeffer et al. |
| 2006/0212111 A1 | 9/2006 | Case et al. |
| 2006/0247570 A1 | 11/2006 | Pokorney |
| 2006/0247763 A1 | 11/2006 | Slater |
| 2006/0253191 A1 | 11/2006 | Salahieh et al. |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010876 A1 | 1/2007 | Salahieh et al. |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Jantz et al. |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi et al. |
| 2007/0100440 A1 | 5/2007 | Figulla et al. |
| 2007/0100449 A1 | 5/2007 | O'Neil et al. |
| 2007/0112415 A1 | 5/2007 | Bartlett |
| 2007/0112422 A1 | 5/2007 | Dehdashtian |
| 2007/0162102 A1 | 7/2007 | Ryan et al. |

(56) References Cited

U.S. PATENT DOCUMENTS

| | | |
|---|---|---|
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0213813 A1 | 9/2007 | Von Segesser et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan et al. |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1* | 6/2008 | Nguyen et al. ............. 623/2.11 |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0021672 A1 | 9/2008 | Lamphere et al. |
| 2008/0215143 A1 | 9/2008 | Seguin |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Sari et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0164006 A1 | 6/2009 | Seguin et al. |
| 2009/0171447 A1 | 7/2009 | Von Segesser et al. |
| 2009/0171456 A1 | 7/2009 | Kveen et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0281619 A1 | 11/2009 | Le et al. |
| 2009/0287296 A1 | 11/2009 | Manasse |
| 2010/0004740 A1 | 1/2010 | Seguin et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0174362 A1 | 7/2010 | Straubinger et al. |
| 2010/0198346 A1 | 8/2010 | Keogh et al. |
| 2010/0234940 A1 | 9/2010 | Dolan |
| 2010/0256723 A1 | 10/2010 | Murray |
| 2010/0292785 A1 | 11/2010 | Sequin et al. |
| 2011/0029066 A1 | 2/2011 | Gilad et al. |
| 2011/0137397 A1 | 6/2011 | Chau et al. |

FOREIGN PATENT DOCUMENTS

| | | |
|---|---|---|
| DE | 19532846 A1 | 3/1997 |
| DE | 19907646 A1 | 8/2000 |
| DE | 10049813 C1 | 4/2002 |
| DE | 19546692 C2 | 11/2002 |
| DE | 10048814 B4 | 4/2004 |
| DE | 10049812 B4 | 6/2004 |
| DE | 10010074 B4 | 4/2005 |
| DE | 19857887 B4 | 5/2005 |
| DE | 10049815 B4 | 10/2005 |
| EP | 0103546 B1 | 5/1988 |
| EP | 144167 B1 | 11/1989 |
| EP | 0850607 A1 | 7/1998 |
| EP | 0597967 B1 | 12/1999 |
| EP | 1057459 A1 | 12/2000 |
| EP | 1057460 A1 | 12/2000 |
| EP | 0937439 B1 | 9/2003 |
| EP | 1340473 A2 | 9/2003 |
| EP | 1356793 A2 | 10/2003 |
| EP | 0819013 B1 | 6/2004 |
| EP | 1229864 B1 | 4/2005 |
| EP | 1000590 B1 | 6/2005 |
| EP | 1088529 B1 | 6/2005 |
| EP | 1469797 B1 | 11/2005 |
| EP | 1255510 B1 | 4/2007 |
| EP | 1600121 B1 | 7/2007 |
| EP | 1472996 B1 | 9/2009 |
| EP | 2257242 | 12/2010 |
| FR | 2788217 A1 | 7/2000 |
| FR | 2815844 A1 | 5/2002 |
| GB | 2056023 A | 3/1981 |
| GB | 2398245 B | 3/2007 |
| GB | 2433700 B | 12/2007 |
| SU | 1271508 A1 | 11/1986 |
| WO | WO 91/17720 A1 | 11/1991 |
| WO | WO 92/17118 A1 | 10/1992 |
| WO | WO 93/01768 A1 | 2/1993 |

(56) References Cited

FOREIGN PATENT DOCUMENTS

| | | |
|---|---|---|
| WO | WO 93/15693 A1 | 8/1993 |
| WO | WO 95/04556 A2 | 2/1995 |
| WO | WO 95/29640 A1 | 11/1995 |
| WO | WO 96/14032 A1 | 5/1996 |
| WO | WO 96/30072 A1 | 10/1996 |
| WO | WO 98/14137 A1 | 4/1998 |
| WO | WO 98/29057 A1 | 7/1998 |
| WO | WO 98/36790 A1 | 8/1998 |
| WO | WO 99/12483 A1 | 3/1999 |
| WO | WO 99/33414 A1 | 7/1999 |
| WO | WO 99/40964 A1 | 8/1999 |
| WO | WO 99/47075 A1 | 9/1999 |
| WO | WO 00/09059 A2 | 2/2000 |
| WO | WO 00/41652 A1 | 7/2000 |
| WO | WO 00/44308 A2 | 8/2000 |
| WO | WO 00/44313 A1 | 8/2000 |
| WO | WO 00/47136 A1 | 8/2000 |
| WO | WO 00/47139 A1 | 8/2000 |
| WO | WO 00/67661 A2 | 11/2000 |
| WO | WO 01/05331 A1 | 1/2001 |
| WO | WO 01/35870 A1 | 5/2001 |
| WO | WO 01/49213 A2 | 7/2001 |
| WO | WO 01/54625 A1 | 8/2001 |
| WO | WO 01/62189 A1 | 8/2001 |
| WO | WO 01/64137 A1 | 9/2001 |
| WO | WO 01/76510 A2 | 10/2001 |
| WO | WO 01/97715 A1 | 12/2001 |
| WO | WO 02/22054 A1 | 3/2002 |
| WO | WO 02/36048 A1 | 5/2002 |
| WO | WO 02/41789 A2 | 5/2002 |
| WO | WO 02/43620 A1 | 6/2002 |
| WO | WO 02/47575 A2 | 6/2002 |
| WO | WO 02/49540 A2 | 6/2002 |
| WO | WO 02/060352 A1 | 8/2002 |
| WO | WO 02/100297 A2 | 12/2002 |
| WO | WO 03/003943 A2 | 1/2003 |
| WO | WO 03/003949 A2 | 1/2003 |
| WO | WO 03/011195 A2 | 2/2003 |
| WO | WO 03/015851 A1 | 2/2003 |
| WO | WO 03/028592 A1 | 4/2003 |
| WO | WO 03/030776 A2 | 4/2003 |
| WO | WO 03/037227 A2 | 5/2003 |
| WO | WO 03/094793 A1 | 11/2003 |
| WO | WO 2004/019811 A2 | 3/2004 |
| WO | WO 2004/019825 A1 | 3/2004 |
| WO | WO 2004/023980 A2 | 3/2004 |
| WO | WO 2004/041126 A1 | 5/2004 |
| WO | WO 2004/047681 A1 | 6/2004 |
| WO | WO 2004/058106 A2 | 7/2004 |
| WO | WO 2004/089250 A1 | 10/2004 |
| WO | WO 2004/089253 A1 | 10/2004 |
| WO | WO 2004/093728 A2 | 11/2004 |
| WO | WO 2004/105651 A1 | 12/2004 |
| WO | WO 2005/002466 A2 | 1/2005 |
| WO | WO 2005/004753 A1 | 1/2005 |
| WO | WO 2005/009285 A2 | 2/2005 |
| WO | WO 2005/011534 A1 | 2/2005 |
| WO | WO 2005/011535 A2 | 2/2005 |
| WO | WO 2005/023155 A1 | 3/2005 |
| WO | WO 2005/027790 A1 | 3/2005 |
| WO | WO 2005/046528 A1 | 5/2005 |
| WO | WO 2006/026371 A1 | 3/2006 |
| WO | WO 2006/070372 A2 | 7/2006 |
| WO | WO 2006/076890 A2 | 7/2006 |
| WO | WO 2007/013999 A2 | 2/2007 |
| WO | WO 2008/047354 A2 | 4/2008 |
| WO | WO 2008/100599 A1 | 8/2008 |
| WO | WO 2008/138584 A1 | 11/2008 |
| WO | WO 2008/150529 A1 | 12/2008 |
| WO | WO 2009/002548 A1 | 12/2008 |
| WO | WO 2009/029199 A1 | 3/2009 |
| WO | WO 2009/042196 A2 | 4/2009 |
| WO | WO 2009/045338 A1 | 4/2009 |
| WO | WO 2009/053497 A1 | 4/2009 |
| WO | WO 2009/061389 A2 | 5/2009 |
| WO | WO 2009/091509 A1 | 7/2009 |
| WO | WO 2009/100198 A2 | 8/2009 |
| WO | WO 2009/108615 A1 | 9/2009 |
| WO | WO 2009/111241 A2 | 9/2009 |
| WO | WO 2010/104638 A2 | 9/2010 |
| WO | WO 2010/141626 A2 | 12/2010 |

OTHER PUBLICATIONS

Babaliaros, V. and Block, P., "State of the Art Percutaneous Intervention for the Treatment of Valvular Heart Disease: A Review of the Current Technologies and Ongoing Research in the Field of Percutaneous Heart Valve Replacement and Repair," *Cardiology* 107:87-96 (2007).

Bailey, S., "Percutaneous Expandable Prosthetic Valves," in *Textbook of Interventional Cardiology*, vol. II, Second edition, 1268-1276, E. Topel ed., WB Saunders, Philadelphia, United States (1994).

Block, P., and Bonhoeffer, P., "Percutaneous Approaches to Valvular Heart Disease," *Current Cardiology Reports* 7:108-113 (2005).

Bonhoeffer, P., et al., "Percutaneous Insertion of the Pulmonary Valve," *Journal of the American College of Cardiology* 39(10):1664-1669, United States (May 15, 2002).

Bonhoeffer, P., et al., "Percutaneous Mitral Valve Dilatation with the Multi-Track System," *Catheterization and Cardiovascular Intervention* 48:178-183, United States (Oct. 1999).

Bonhoeffer, P., et al., "Percutaneous Replacement of Pulmonary Valve in a Right-Ventricle to Pulmonary-Artery Prosthetic Conduit with Valve Dysfunction," *The Lancet* 356:1403-1405, England (Oct. 21, 2000).

Bonhoeffer, P., et al., "Technique and Results of Percutaneous Mitral Valvuloplasty With the Multi-Track System," *Journal of Interventional Cardiology* 13(4):263-268, United States (2000).

Bonhoeffer, P., et al., "Transcatheter Implantation of a Bovine Valve in Pulmonary Position: A Lamb Study," *Circulation* 102:813-816, United States (Aug. 15, 2000).

Boudjemline, Y., and Bonhoeffer, P., "Percutaneous Aortic Valve Replacement in Animals," *Circulation* 109:e161, United States, (Mar. 16, 2004).

Boudjemline, Y., and Bonhoeffer, P., "Is Percutaneous Implantation of a Bovine Venous Valve in the Inferior Vena Cava a Reliable Technique to Treat Chronic Venous Insufficiency Syndrome?" *Medical Science Monitor-International Medical Journal of Experimental and Clinical Research* 10(3):BR61-BR66, Poland, (Mar. 2004).

Boudjemline, Y., et al., "Off-pump Replacement of the Pulmonary Valve in Large Right Ventricular Outflow Tracts: A Hybrid Approach," *The Journal of Thoracic and Cardiovascular Surgery* 129(4):831-837, United States (Apr. 2005).

Boudjemline, Y., et al., "Percutaneous Aortic Valve Replacement: Will We Get There?" *Heart* 86:705-706, British Cardiac Society, England (Dec. 2001).

Boudjemline, Y., et al., "Percutaneous Closure of a Paravalvular Mitral Regurgitation with Amplatzer and Coil Prostheses," *Archives des Maladies du Coeur Et Des Vaisseaux*:483-486, France (May 2002).

Boudjemline, Y., et al., "Percutaneous Implantation of a Biological Valve in Aortic Position: Preliminary Results in a Sheep Study," *European Heart Journal* 22:630 (Sep. 2001).

Boudjemline Y., et al., "Percutaneous Implantation of a Biological Valve in the Aorta to Treat Aortic Valve Insufficiency—A Sheep Study," *Medical Science Monitor-International Medical Journal of Experimental and Clinical Research* 8(4):BR 113-BR116, Poland (Apr. 2002).

Boudjemline, Y., and Bonhoeffer, P., "Percutaneous Implantation of a Valve in the Descending Aorta in Lambs," *European Heart Journal* 23:1045-1049, England (Jul. 2002).

Boudjemline, Y., et al., "Percutaneous Pulmonary Valve Replacement in a Large Right Ventricular Outflow Tract: An Experimental Study," *Journal of the American College of Cardiology* 43(6):1082-1087, United States (Mar. 17, 2004).

(56) References Cited

OTHER PUBLICATIONS

Boudjemline, Y., et al., "Percutaneous Valve Insertion: A New Approach?," *The Journal of Thoracic and Cardiovascular Surgery* 125(3):741-742, United States (Mar. 2003).
Boudjemline, Y., et al., "Stent Implantation Combined with a Valve Replacement to Treat Degenerated Right Ventricle to Pulmonary Artery Prosthetic Conduits," *European Heart Journal* 22:355 (Sep. 2001).
Boudjemline, Y., and Bonhoeffer, P., "Steps Toward Percutaneous Aortic Valve Replacement," *Circulation* 105:775-778, United States (Feb. 12, 2002).
Boudjemline, Y., and Bonhoeffer, P., "The Percutaneous Implantable Heart Valve," *Progress in Pediatric Cardiology* 14:89-93, Ireland, (2001).
Boudjemline, Y., et al., "Transcatheter Reconstruction of the Right Heart," *Cardiology in the Young* 13:308-11, England (Jun. 2003).
Coats, L., et al., "The Potential Impact of Percutaneous Pulmonary Valve Stent Implantation on Right Ventricular Outflow Tract Re-Intervention," *European Journal of Cardio-Thoracic Surgery* 27:536-543, England (Apr. 2005).
Commeau, P., et al., "Percutaneous balloon dilatation of calcific aortic valve stenosis: anatomical and haemodynamic evaluation," *British Heart Journal* 59:227-238 (1988).
Cribier, A. et al., "Percutaneous Transcatheter Implantation of an Aortic Valve Prosthesis for Calcific Aortic Stenosis: First Human Case Description," *Circulation* 106:3006-3008 (2002).
Davidson, M., et al., "Percutaneous therapies for valvular heart disease," *Cardiovascular Pathology* 15:123-129 (2006).
Deac, R. et al., "New evolution in mitral physiology and surgery: mitral stentless pericardial valve," *Ann. Thorac. Surg.* 60(2 Suppl):S433-S438 (Aug. 1995).
Hanzel, G., and O'Neill., W., "Complications of percutaneous aortic valve replacement: experience with the Criber-Edwards™ percutaneous heart valve," *EuroIntervention Supplements I (Supplement A)*:A3-A8 (2006).
Heinrich, R. et al., "Experimental analysis of fluid mechanical energy losses in aortic valve stenosis: importance of pressure recovery," *Ann. Biomed. Eng.* 24:685-694 (Nov.-Dec. 1996).
Heinrich, R. et al., "Valve orifice area alone is an insufficient index of aortic stenosis severity: effects of the proximal and distal geometry on transaortic energy loss," *J. Heart Valve Dis.* 8(5):509-515, Abstract, (Sep. 1999).
Huber, C., et al., "Do Valved Stents Compromise Coronary Flow?" *Eur. J. Cardiothorac. Surg.* 25:754-759 (2004).
Khambadkone, S., and Bonhoeffer, P., "Percutaneous Implantation of Pulmonary Valves." *Expert Review of Cardiovascular Therapy*:541-548, England (Nov. 2003).
Khambadkone, S., et al., "Percutaneous Pulmonary Valve Implantation: Early and Medium Term Results," *Circulation* 108 (17 Supplement):IV-375 (Oct. 28, 2003).
Khambadkone, S., et al.,"Percutaneous Pulmonary Valve Implantation: Impact of Morphology on Case Selection," *Circulation* 108 (17 Supplement):IV-642-643 (Oct. 28, 2003).
Khambadkone, S., and Bonhoeffer, P., "Nonsurgical Pulmonary Valve Replacement: Why, When, and How?" *Catheterization and Cardiovascular Interventions* 62:401-408, United States (Jul. 2004).
Lutter, G., et al., "Percutaneous Aortic Valve Replacement: An Experimental Study," *The Journal of Thoracic and Cardiovascular Surgery* 123(9):768-776 (Apr. 2002).
Lutter, G., et al., "Percutaneous Valve Replacement: Current State and Future Prospects," *Annals of Thoracic Surgery* 78:2199-2206, Netherlands (Dec. 2004).
Ma, L. et al., "Double-crowned valved stents for off-pump mitral valve replacement," *European Journal of Cardio-Thoracic Surgery* 28:194-198 (2005).
Marcus, R. et al., "Assessment of small-diameter aortic mechanical prostheses: physiological relevance of the Doppler gradient, utility of flow augmentation, and limitations of orifice area estimation," *Circulation* 98(9):866-872 (Sep. 1, 1998).

"New Frontiers in Heart Valve Disease," *Medtech Insight* 7(8) (Aug. 2005).
Niethspach, F., et al., "Current Balloon-Expandable Transcatheter Heart Valve and Delivery Systems," *Catheterization and Cardiovascular Interventions*:1-6 (2009).
Palacios, I., "Percutaneous Valve Replacement and Repair, Fiction or Reality?" *Journal of American College of Cardiology* 44(8):1662-1663 (2004).
Pavcnik, P., et al., "Aortic and venous valve for percutaneous insertion," *Min. Invas. Ther. & Allied Techol.* 9(3/4):287-292 (2000).
Pelton, A.R., et al., "Medical Uses of Nitinol," *Materials Science Forum* 327-328:63-70 (2000).
Ruiz, C.E., "Transcathether Aortic Valve Implantation and Mitral Valve Repair: State of the Art," *Pediatric Cardiology* 26(3):289-294 (2005).
Saliba, Z., et al., "Treatment of Obstructions of Prosthetic Conduits by Percutaneous Implantation of Stents," *Archives des Maldies du Coeur et des Vaisseaux* 92(5):591-596, France (1999).
Stassano, P., et al., "Mid-term results of the valve-on-valve technique for bioprosthetic failure," *Eur. J. Cardiothorac. Surg.* 18:453-457 (2000).
Stein, P., and Sabbah. H.N., "Turbulent blood flow in the ascending aorta of humans with normal and diseased aortic valves," *Circulation Research* 39:58-65, American Heart Association (1976).
Webb, J., et al., "Percutaneous Aortic Valve Implantation Retrograde from the Femoral Artery," *Circulation* 113:842-850 (2006).
Weyman, A., and Scherrer-Crosbie, M., "Aortic Stenosis: Physics and Physiology—What Do the Numbers Really Mean?," *Rev. Cardiovasc. Med.* 6(1):23-32 (2005).
Yonga, G.O., et al., "Effect of Percutaneous Balloon Mitral Valvotomy on Pulmonary Venous Flow in Severe Mitral Stenosis," *East African Medical Journal* 76(1):28-30, Kenya (Jan. 1999).
Yonga, G.O., et al., "Percutaneous Balloon Mitral Valvotomy: Initial Experience in Nairobi Using a New Multi-Track Catheter System," *East African Medical Journal* 76(2):71-74, Kenya (Feb. 1999).
Yonga, G.O., et al., "Percutaneous Transluminal Balloon Valvuloplasty for Pulmonary Valve Stenosis: Report on Six Cases," *East African Medical Journal* 71(4):232-235, Kenya (Apr. 1994).
Yonga, G.O, and Bonhoeffer, P., "Percutaneous Transvenous Mitral Commissurotomy in Juvenile Mitral Stenosis," *East African Medical Journal* 80(4): 172-174, Kenya, (Apr. 2003).
English Language Abstract of German Patent Publication No. DE 10049812 B4, European Patent Office, espacenet database—Worldwide, (2004).
English Language Abstract of German Patent Publication No. DE 10049813 C1, European Patent Office, espacenet database—Worldwide, (2002).
English Language Abstract of German Patent Publication No. DE 10049815 B4, European Patent Office, espacenet database—Worldwide, (2005).
English Language Abstract of German Patent Publication No. DE 19532846 A1, European Patent Office, espacenet database—Worldwide, (1997).
English Language Abstract of German Patent Publication No. DE 19546692 C2, European Patent Office, espacenet database—Worldwide, (2002).
English Language Abstract of German Patent Publication No. DE 19857887 B4, European Patent Office, espacenet database—Worldwide, (2005).
English Language Abstract of German Patent Publication No. DE 19907646 A1, European Patent Office, espacenet database—Worldwide, (2000).
English Language Abstract of Chinese Patent Publication No. 101011298 A, European Patent Office, espacenet database—Worldwide, (2007).
Drawing by Dr. Buller (Edwards Expert) of "higher stent" on the schematic representation of the aortic valve area set out in Figure 2 of Rothman's first expert report, *Corevalve, Inc. v. Edwards Lifesciences AG and Edwards Lifesciences PVT, Inc.*, High Court of Justice—Chancery Division Patents Court, United Kingdom, Case No. HC-07-001243.

(56) References Cited

OTHER PUBLICATIONS

Drawing by Dr. Buller (Edwards Expert) of his interpretation of the "higher stent" referred to at col. 8, lines 13-222 of Andersen EP 592410B1, *Corevalve, Inc.* v. *Edwards Lifesciences AG and Edwards Lifesciences PVT Inc.*, High Court of Justice—Chancery Division Patents Court, United Kingdom, Case No. HC-07-C01243.
Expert report of Dr. Nigel Buller, *Edwards Lifesciences AG* v. *Cook Biotech Incorporated*, High Court of Justice—Chancery Division Patents Court, United Kingdom, Case No. HC 08CO0934.
Expert report of Dr. Nigel Buller, non-confidential annex—infringement, *Edwards Lifesciences AG* v. *Cook Biotech Incorporated*, High Court of Justice—Chancery Division Patents Court, United Kingdom, Case No. HC 08CO0934.
Expert report of Dr. Rodolfo Quijano, *Edwards Lifesciences AG* v. *Cook Biotech Incorporated*, High Court of Justice—Chancery Division Patents Court, United Kingdom, Case No. HC 08CO0934.
First Expert report of Dr. Anthony C. Lunn, *Corevalve, Inc.* v. *Edwards Lifesciences AG and Edwards Lifesciences PVT, Inc.*, High Court of Justice—Chancery Division Patents Court, United Kingdom, Case No. HC-07-C01243.
First Expert report of Dr. Nigel Person Buller, *Corevalve, Inc.* v. *Edwards Lifesciences AG and Edwards Lifesciences PVT, Inc.*, High Court of Justice—Chancery Division Patents Court, United Kingdom, Case No. HC-07-C01243.
First Expert report of Prof. David Williams, *Edwards Lifesciences AG* v. *Cook Biotech Incorporated*, High Court of Justice—Chancery Division Patents Court, United Kingdom, Case No. HC 08CO0934.
First Expert report of Prof. Martin Rothman, *Edwards Lifesciences AG* v. *Cook Biotech Incorporated*, High Court of Justice—Chancery Division Patents Court, United Kingdom, Case No. HC 08CO0934.
First Expert report of professor John R. Pepper, *Corevalve, Inc.* v. *Edwards Lifesciences AG and Edwards Lifesciences PVT, Inc.*, High Court of Justice—Chancery Division Patents Court, United Kingdom, Case No. HC-07-C01243.
First Expert report of Professor Martin Terry Rothman, *Corevalve, Inc.* v. *Edwards Lifesciences AG and Edwards Lifesciences PVT, Inc.*, High Court of Justice—Chancery Division Patents Court, United Kingdom, Case No. HC-07-C01243.
First Expert report of Richard A. Hillstead, *Corevalve, Inc.* v. *Edwards Lifesciences AG and Edwards Lifesciences PVT, Inc.*, High Court of Justice—Chancery Division Patents Court, United Kingdom, Case No. HC-07-C01243.
First Witness statement of Stanton Rowe, *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Fourth Expert report of Prof. Martin Rothman, *Edwards Lifesciences AG* v. *Cook Biotech Incorporated*, High Court of Justice—Chancery Division Patents Court, United Kingdom, Case No. HC 08CO0934.
PVT slides naming Alain Cribier, Martin Leon, Stan Rabinovich and Stanton Rowe, *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Reply Expert report of Professor Martin Terry Rothman, *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Reply Expert report of Richard A. Hillstead, *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Second Expert report of Dr. Nigel Buller, *Edwards Lifesciences AG* v. *Cook Biotech Incorporated*, High Court of Justice—Chancery Division Patents Court, United Kingdom, Case No. HC 08CO0934.
Second Expert report of Dr. Nigel Buller, dated May 27, 2008, *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Second Expert report of Dr. Rodolfo Quijano, *Edwards Lifesciences AG* v. *Cook Biotech Incorporated*, High Court of Justice—Chancery Division Patents Court, United Kingdom, Case No. HC 08CO0934.
Second Expert report of Prof. David Williams, *Edwards Lifesciences AG* v. *Cook Biotech Incorporated*, High Court of Justice—Chancery Division Patents Court, United Kingdom, Case No. HC 08CO0934.
Second Expert report of Prof. Martin Rothman, *Edwards Lifesciences AG* v. *Cook Biotech Incorporated*, High Court of Justice—Chancery Division Patents Court, United Kingdom, Case No. HC 08CO0934.
Second Expert report of Professor John R. Pepper, *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Second Witness statement of Stanton Rowe, *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Third Expert report of Dr. Nigel Buller, *Edwards Lifesciences AG* v. *Cook Biotech Incorporated*, High Court of Justice—Chancery Division Patents Court, United Kingdom, Case No. HC 08CO0934.
Third Expert report of Dr. Rudolfo Quijano, *Edwards Lifesciences AG* v. *Cook Biotech Incorporated*, High Court of Justice—Chancery Division Patents Court, United Kingdom, Case No. HC 08CO0934.
Third Expert report of Prof. David Williams, *Edwards Lifesciences AG* v. *Cook Biotech Incorporated*, High Court of Justice—Chancery Division Patents Court, United Kingdom, Case No. HC 08CO0934.
Lutter, et al., "Off-Pump Transapical Mitral Valve Replacement" Eur J Cardiothorac Surg 2009;36: 124-128.

\* cited by examiner

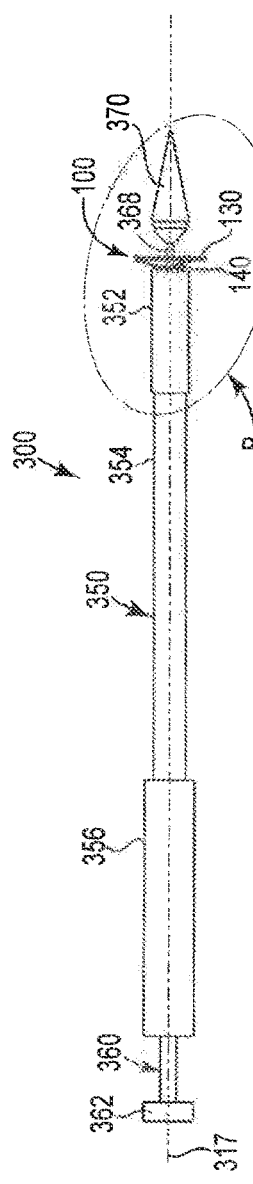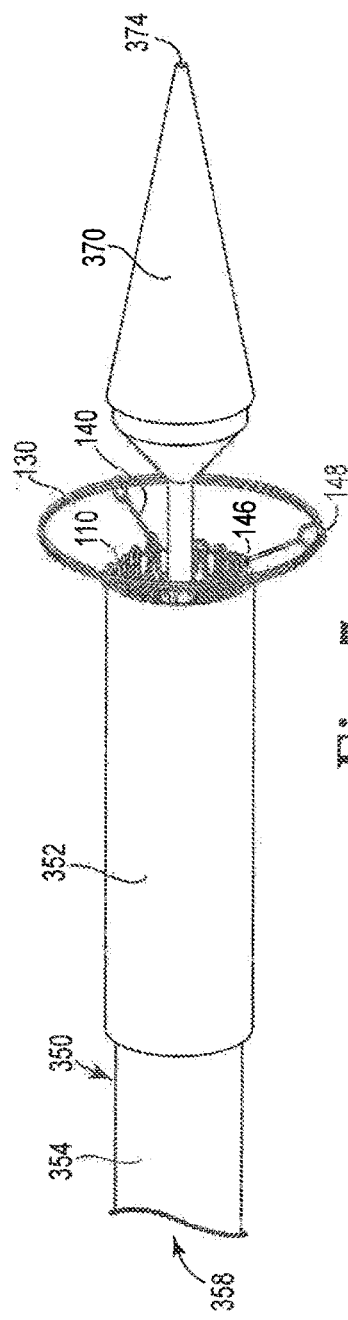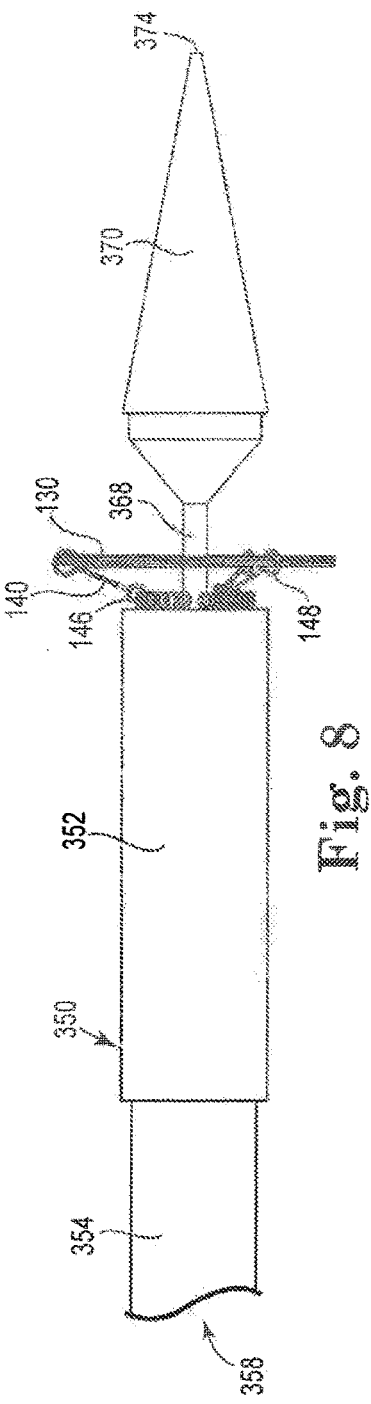

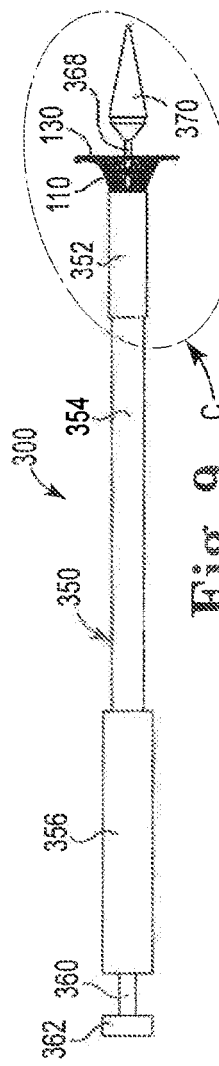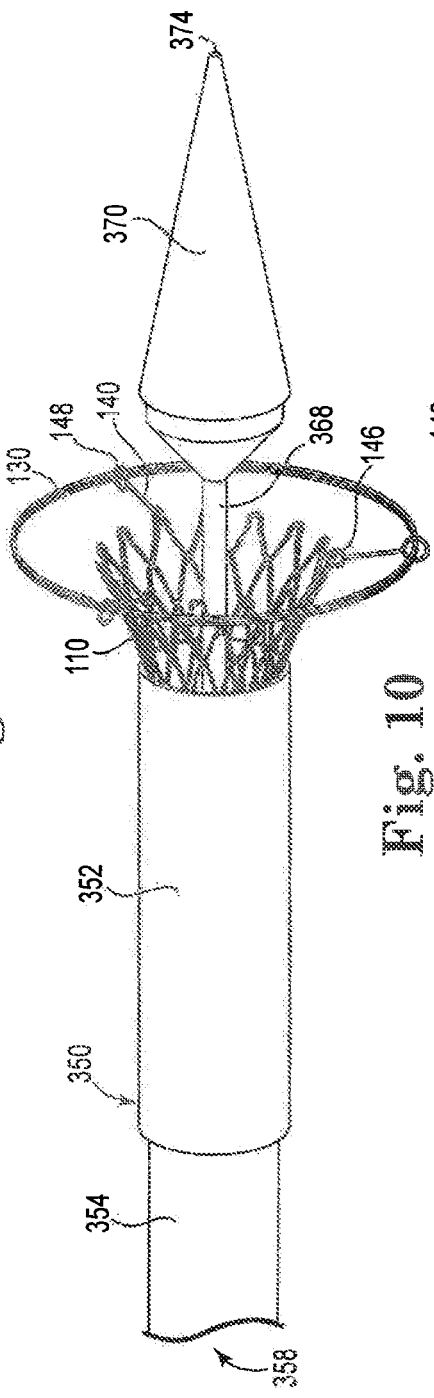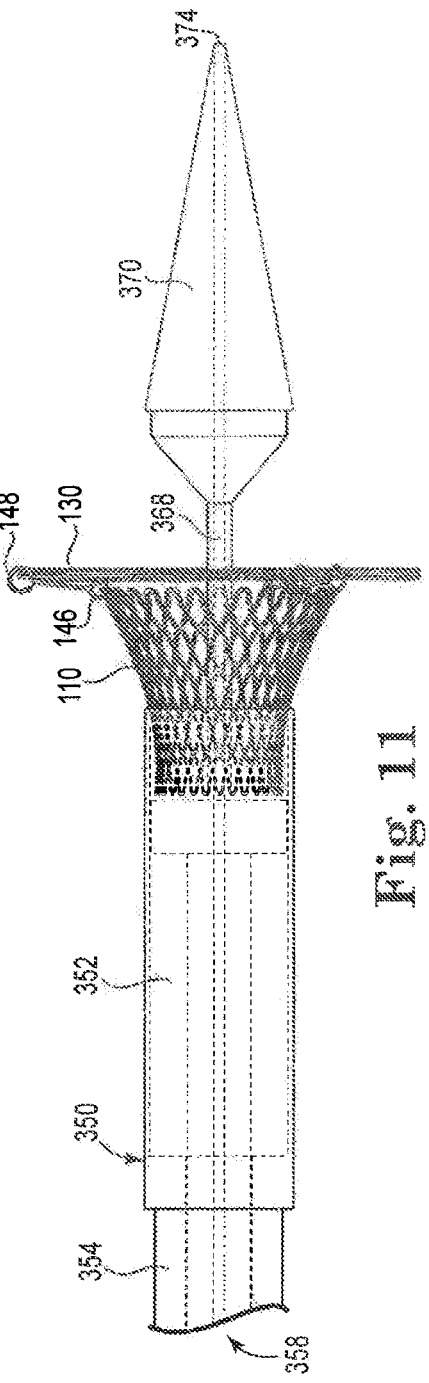

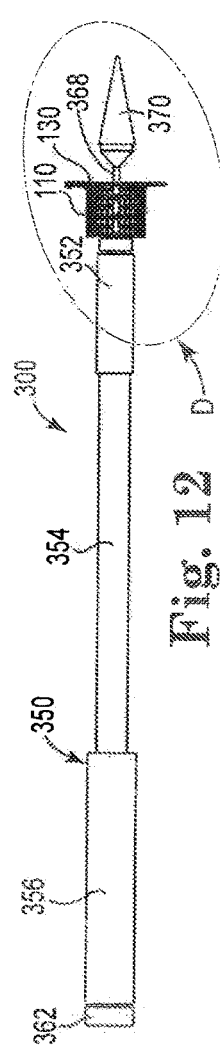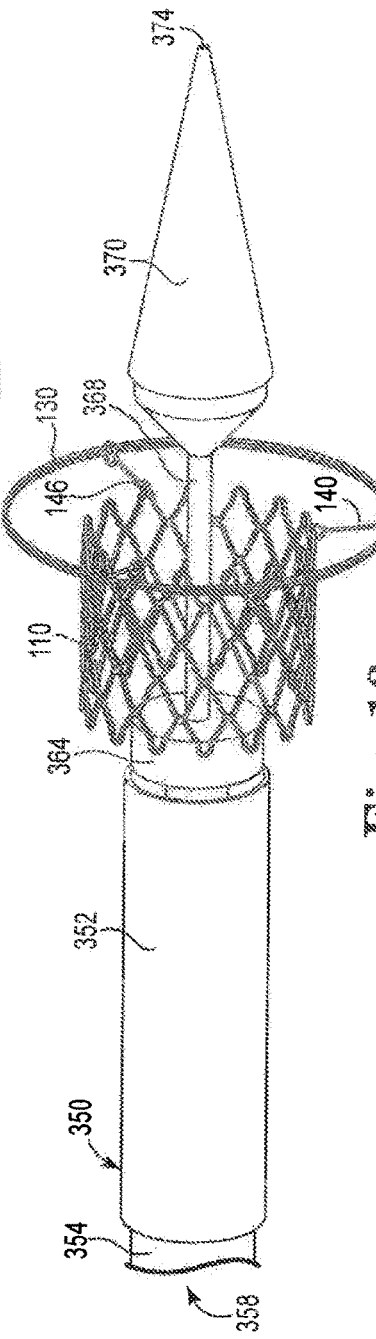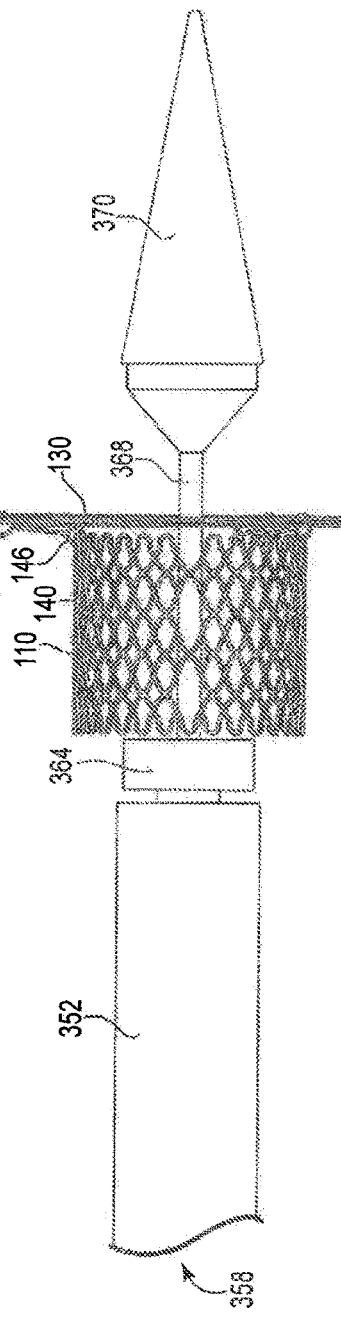

TRANSCATHETER VALVE WITH TORSION SPRING FIXATION AND RELATED SYSTEMS AND METHODS

CROSS REFERENCE TO RELATED APPLICATION

This application is a continuation of U.S. application Ser. No. 12/846,962, filed Jul. 30, 2010, now U.S. Pat. No. 8,652,204, which is incorporated herein by reference in its entirety, and which claims the benefit under 35 U.S.C. § 119(e) of U.S. Provisional Patent Application No. 61/320,111, filed Apr. 1, 2010, which is incorporated herein by reference in its entirety.

FIELD OF THE INVENTION

The invention relates generally to medical devices, systems and methods for use in a body (e.g., in a cardiac system), and more particularly, to devices, systems and methods for minimally invasive native heart valve replacement.

BACKGROUND OF THE INVENTION

Natural heart valves, such as aortic valves, mitral valves, pulmonary valves and tricuspid valves, can become damaged by disease in such a manner that they fail to maintain blood flow in a single direction. A malfunctioning heart valve may be stenotic (i.e., heart leaflets are closed down) or regurgitant (i.e., heart leaflets are wide open). Maintenance of blood flow in a single direction through the heart valve is important for proper flow, pressure and perfusion of blood through the body. Hence, a heart valve that does not function properly may noticeably impair the fraction of the heart.

Cardiac valve prostheses are well known in the treatment of heart disease to replace malfunctioning heart valves. Heart valve replacement previously required open-heart surgery with its attendant risk, expense, and extended recovery time. Open-heart surgery also requires cardiopulmonary bypass with risk of thrombosis, stroke and infarction. For some patients, open-heart surgery is not even an option because of a critical condition, advanced age, co-existing infection, or other physical limitations.

Recently, there has been increasing interest in minimally invasive and percutaneous replacement of cardiac valves, typically by way of catheterization. In minimally invasive procedures, a catheter is used to insert a valve in a lumen of a blood vessel via percutaneous entry through a distal blood vessel. Typically, such percutaneous prosthetic valve devices comprise an expandable stent segment, a stent anchoring segment and a flow-regulation segment, such as a biological valve. The expandable stent portion is either self-expandable or expanded using a balloon that is part of a transcatheter delivery system.

A drawback of using a stented valve is that the stein can be difficult to properly position, resulting in a misplaced valve. Additionally, stented valves may also lack sufficient radial strength, which could cause migration after implantation due to forces applied by the blood surrounding the valve in the heart. Therefore, there is a need for improved heart valve prostheses that may be implanted using minimally invasive techniques.

SUMMARY OF THE INVENTION

The invention has advantages over prior devices, systems and methods. The invention mitigates the potential complications of invasive surgery, by applying minimally invasive techniques to replace a damaged or malfunctioning heart valve with a replacement prosthetic heart valve. The invention allows for proper placement of the prosthetic heart valve. The inventive prosthetic heart valve is configured to include an amount of radial force in order to keep the prosthetic heart valve in contact with a body lumen into which the valve is implanted. The inventive prosthetic heart valve also reduces or eliminates sliding or migration of the prosthetic heart valve. One benefit to reducing migration of the prosthetic heart valve is that the device is able to perform its intended function, which allows the heart to function properly. Another benefit of eliminating migration of the prosthetic heart valve is that additional surgeries are not required to repair or replace the valve.

One aspect of the invention is a prosthetic valve. The prosthetic valve may comprise: an expandable stent including an inner lumen and having a first and a second end; and a spring attached to the first end of the expandable stent; wherein the expandable stent and the spring can expand radially to a desired diametric configuration in order to anchor the prosthetic valve at an implantation position in a body lumen. The prosthetic valve may further comprise a valvular element disposed in the inner lumen of the expandable stent. The valvular element may comprise at least one leaflet. The prosthetic valve may further comprise a plurality of support arms that are used to attach the spring to the first end of the expandable stent. Each of the plurality of support arms may comprise at least one loop through which the spring extends and is attached to the support arm. The support arms may comprise a material that is more stiff than a material comprising the spring. The support arms may limit the amount of radial expansion of the spring in order to result in a desired diametric configuration of the spring. The spring may comprise a torsion spring. The expandable stent may be sized to fit in a heart valve selected from a group consisting of an aortic valve, a mitral valve, a tricuspid valve, and a pulmonary valve. The spring and the expandable stent may be compressed into a collapsed position for insertion into a sheath for delivery to the implantation position. The prosthetic valve may further comprise a second spring attached to the second end of the expandable stent.

A second aspect of the invention is a prosthetic valve delivery system. The system may comprise: a prosthetic valve, comprising: an expandable stent including an inner lumen and having a first and a second end; a valvular element disposed in the inner lumen of the expandable stent; and a spring attached to the first end of the expandable stent; wherein the expandable stent and the spring can expand radially to a desired diametric configuration once deployed in order to anchor the prosthetic valve at an implantation position in a body lumen; and a sheath comprising a distal end and a lumen in which the prosthetic valve is positioned prior to deployment of the prosthetic valve and out of which the prosthetic valve is deployed at the implantation position. The sheath may be retractable in order to deploy the prosthetic valve.

A third aspect of the invention is a method of implanting a prosthetic valve. The method may comprise the steps of: inserting a system into a body, the system comprising: a prosthetic valve, comprising: an expandable gent including an inner lumen and having a first and a second end; a valvular element disposed in the inner lumen of the expandable stent; and a spring attached to the first end of the expandable stent; wherein the expandable stent and the spring can expand radially to a desired diametric configuration once deployed in order to anchor the prosthetic valve at an implantation position in a body lumen; and a sheath comprising a distal end and a lumen in which the prosthetic valve is positioned prior to deployment of the prosthetic valve and out of which the prosthetic valve is deployed at the implantation position; advancing the system to the implantation position; and deploying the prosthetic valve to the desired diametric configuration to anchor the prosthetic valve at the implantation position. The sheath may be retractable in order to deploy the prosthetic valve. The method may further comprise the step of pulling proximally on the system when the prosthetic valve is partially deployed. The method may further comprise the step of removing the remainder of the system and leaving the prosthetic valve, once deployed, in place.

BRIEF DESCRIPTION OF THE DRAWINGS

The invention will be apparent from the following detailed description of the invention in conjunction with the accompanying drawings, of which:

FIG. 6 illustrates a side view of the system of FIG. 3 at a later stage in delivery of a prosthetic heart valve of the system;

FIG. 7 illustrates a perspective view of distal end portion B of the system shown in FIG. 6;

FIG. 8 illustrates a side view of distal end portion B of the system shown in FIG. 6;

FIG. 9 illustrates a side view of the system of FIGS. 3 and 6 at a later stage in delivery of the prosthetic heart valve of the system;

FIG. 10 illustrates a perspective view of distal end portion C of the system shown in FIG. 9;

FIG. 11 illustrates a side view of distal end portion C of the system shown in FIG. 9, with interior shown in shadow;

FIG. 12 illustrates a side view of the system of FIGS. 3 and 9 at a later stage in delivery of the prosthetic heart valve of the system;

FIG. 13 illustrates a perspective view of distal end portion D of the system shown in FIG. 12;

FIG. 14 illustrates a side view of distal end portion D of the system shown in FIG. 12;

DETAILED DESCRIPTION OF THE INVENTION

The invention will be described with reference to FIGS. 1-20, wherein like numbers refer to like structures. Those skilled in the art will appreciate that the description herein with respect to the figures is for exemplary purposes only and is not intended in any way to limit the scope of the invention.

Figure 1:
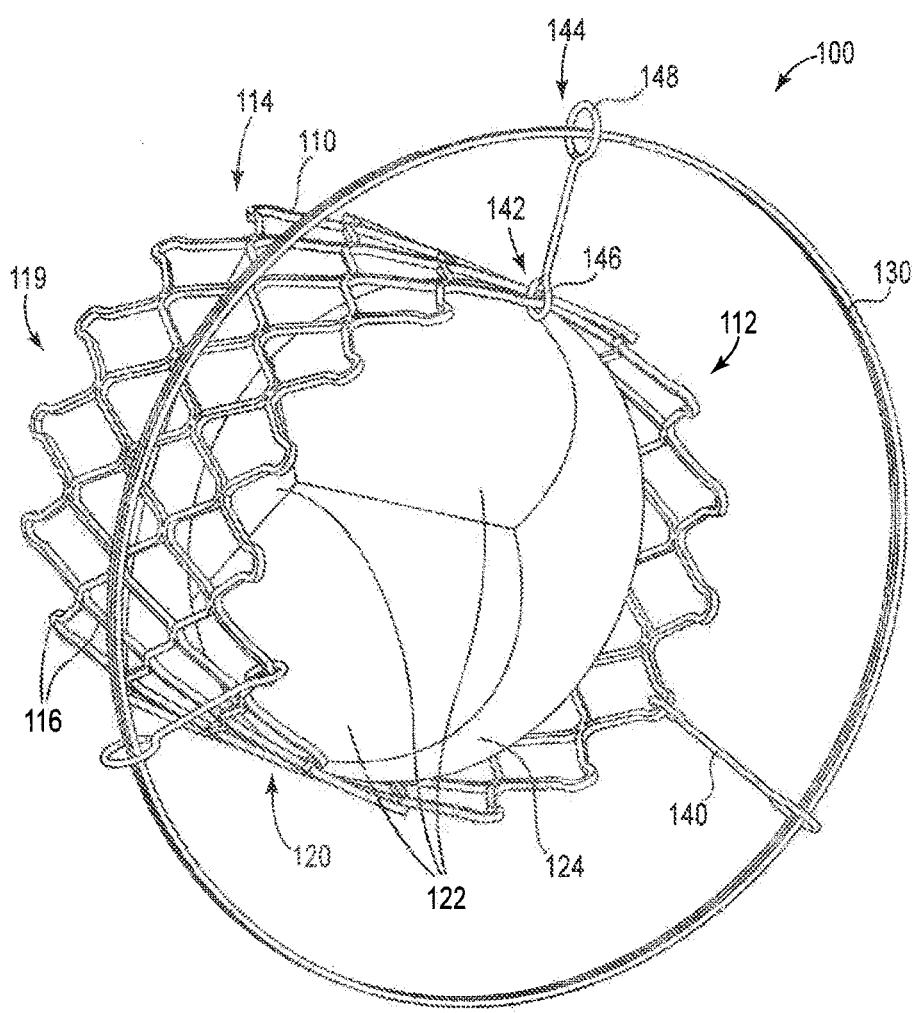
FIG. 1 illustrates a perspective view of an embodiment of a prosthetic heart valve, in accordance with the invention.
Figure 2:
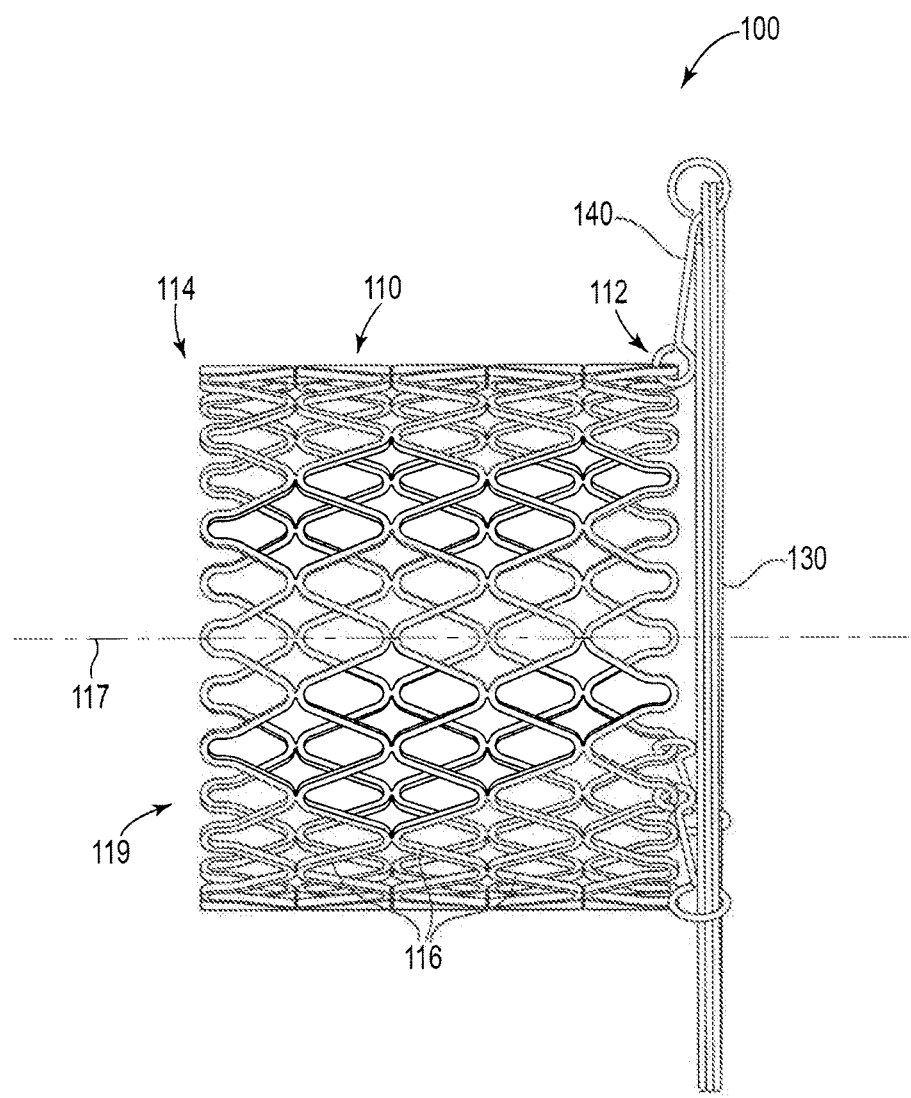
FIG. 2 illustrates a side view of the prosthetic heart valve of FIG. 1.

The invention discloses devices, systems and methods for minimally invasive surgical placement (e.g., via percutaneous catheter placement) of prosthetic heart valves, such as those shown in FIGS. 1 and 2. The invention contemplates that the inventive prosthetic heart valves, systems and methods described herein may be used for replacement of several different heart valves (e.g., mitral valve, tricuspid valve, aortic valve, etc.). More generally, the prosthetic heart valve of the invention may be implanted within a fluid passageway of a body lumen, for example, for replacement or augmentation of a valve structure (e.g., mitral valve), to regulate flow of bodily fluid preferably in a single direction. The invention also contemplates prosthetic valves, in general, that may be used in other suitable locations in the body other than in and near the heart.

One challenge in implanting a prosthetic heart valve within the heart and at a particular annulus is correct placement of the device. Improper placement may cause malfunctioning of the prosthetic heart valve and may require a patient to undergo an additional surgery. The invention addresses this problem by allowing for proper placement of the prosthetic heart valve. In particular, the inclusion of an expandable torsion spring within a prosthetic valve improves the ability to properly place the prosthetic heart valve.

Under certain conditions or due to an improper fit, for example, a prosthetic heart valve may migrate or move after implantation or throughout the life of the prosthetic heart valve due to the forces relating to inflow and backflow of blood flow to and through the prosthetic heart valve. Migration can result in an inadequate seal between the prosthetic heart valve and the wall of the conduit, lumen or vessel, which can further lead to loss of the ability to function effectively. The invention also addresses this problem by inhibiting such migration. Inclusion of an expandable torsion spring within a prosthetic valve for fixation purposes decreases the chances that the prosthetic heart valve migrate.

Referring to the drawings, FIGS. 1 and 2 show a perspective and a side view, respectively, of an embodiment of a prosthetic heart valve of the invention. Prosthetic heart valve 100, as shown, comprises: an expandable stent 110 including an inner lumen 119 and having a first end 112 and a second end 114; and a spring 130 attached to the first end 112 of the expandable stent 110. The expandable stent 110 and the spring 130 can expand radially to a desired diametric configuration in order to anchor the prosthetic valve 100 at an implantation position in a body lumen. FIG. 1 shows the expanded prosthetic valve 100 including a valvular element 120.

The expandable stent 110 preferably defines a generally cylindrical body having first end 112 and second end 114. However, it is contemplated that the expandable stent 110 can have any geometric shape (e.g., cylindrical, conical, spherical, or barrel-like) that is compatible with the placement of the expandable stent 110 within a body lumen.

The expandable stent 110, once deployed, expands to at least the dimension or diameter of a body lumen into which the expandable stent 110 is implanted. Preferably, the expandable stent, when being used in a mitral valve, can have a diameter or diameters from about five (5) millimeters (mm) to about twenty-five (25) millimeters (mm) based upon typical heart anatomical dimensions. However, other dimensions are also contemplated based upon atypical heart anatomical dimensions as well as based upon different valve annuli (e.g., tricuspid, etc.) into which the prosthetic valve may be implanted.

The expandable stent 110 preferably comprises a mesh. The mesh preferably comprises a plurality of wires 116 or strips that comprise a flexible, biocompatible material. Examples of possible materials for the mesh of the expandable stent 110 include those formed from temperature-sensitive memory alloys, which change shape at a designated temperature or temperature range. Alternatively, the expandable stent 110 can be made from a material having a spring bias. Examples of suitable materials include, but are not limited to, medical grade stainless steel (e.g., 316L), titanium, tantalum, platinum alloys, niobium alloys, cobalt alloys, alginate or combinations thereof. Examples of shape-memory materials include shape memory plastics, polymers, and thermoplastic materials, which are inert in the body. Shape memory alloys having superelastic properties generally made from ratios of nickel and titanium, commonly known as Nitinol™, are preferred materials The preferred material for the plurality of wires 116 will have an adequate amount of stiffness to ensure that the expandable stent 110 maintains a desired shape. The stiffness also needs to be adequate so that the expandable stent 110 maintains a desired shape that ensures that leaflets (as discussed below) in the device 100 close and open properly. Sufficient stiffness also can ensure that there will be no paravalvular leakage; in other words, no leaking between the prosthetic heart valve 100 and the body lumen into which it is implanted. Portions of the expandable stent 110 may be made of different materials and may have different amounts of stiffness.

Various patterns of the plurality of wires 116 in the mesh of the expandable stent 110 are possible. The invention is not limited to the patterns shown herein. The preferred pattern will accommodate the shape of the body lumen or annulus into which the expandable stent 110 will be implanted, as well allow for proper expansion of the expandable stent 110 in the body lumen or annulus.

The plurality of wires 116 of the expandable stent 110 can also have a variety of possible cross-sectional geometries. Examples of cross-sectional geometries include, but are not limited to, rectangular, non-planar configurations, round (e.g., circular, oval and/or elliptical), polygonal, arced and tubular.

The expandable stent 110 of the device 100 is able to be reduced in diameter, mounted in a catheter and advanced through the circulatory system or through other ports or incisions into a patient. The expandable stent 110 is preferably self-expanding. However, it is also possible that the expandable stent 110 may be expanded using a balloon or some other suitable method.

The expandable stent 110 defines a lumen 119 or other housing in which valvular element 120 may be disposed. The valvular element 120 preferably comprises valve leaflets 122 coupled to a valve support 124 that fits in the stent 110, with both components being made of any suitable biocompatible material.

The leaflets 122 and support 124 can be derived from autologous, allogenic, or xenograft material. As will be appreciated, sources for xenograft materials (e.g., cardiac valves) include, but are not limited to, mammalian sources, such as porcine, equine, bovine and sheep. Additional biologic materials from which to form the valve leaflets include, but are not limited to, explanted veins, pericardium, fascia lata, harvested cardiac valves, bladder, vein wall, various collagen types, elastin, intestinal submucosa, and decellularized basement membrane materials, such as small intestine submucosa (SIS), amniotic tissue, or umbilical vein.

Alternatively, the leaflets 122 and support 124 can be formed from a synthetic material. Possible synthetic materials include, but are not limited to, expanded polytetrafluoroethylene (ePTFE), polytetrafluoroethylene (PTFE), poly-styrene-poly-isobutylene-polystyrene (SIBS), polyurethane, segmented poly(carbonate-urethane), polyester, polyethylene (PE), polyethylene terephthalate (PET), silk, urethane, rayon, silicone, or the like. In an additional embodiment, the synthetic material can also includes metals, such as stainless steel (e.g., 316L), and Nitinol™. These synthetic materials can be in a woven, a knit, a cast, or other known physical fluid-impermeable or permeable configuration. In addition, plated metals (e.g., gold, platinum, rhodium) can be embedded in the leaflet material (e.g., a sandwich configuration) to allow for visualization of the leaflets 122 post placement.

The leaflets 122 and support 124 can also be formed of any combination of these exemplary materials, or these materials in combination with other materials, as are known in the art. A variety of known treatments and/or coatings can also be included in/on the leaflets 122 and support 124.

The leaflets 122 may comprise a supple and reinforced tissue which is a thickness to be thin enough to occupy the least possible space in the compressed form of the valve, is pliable, and also is strong enough to withstand the unceasing movement under the blood pressure changes during heart beats. The leaflets 122 are capable of moving from a closed position to an open position under the action of the force exerted by the movement of the blood during systole and disastole, without having any significant resistance to blood displacements. The valve leaflets 122 have surfaces defining a reversibly sealable opening for unidirectional flow of a liquid through the prosthetic heart valve 100.

The number of leaflets 122 in the valvular element 120 may be dependent upon the body lumen or annulus into which the prosthetic heart valve 100 is intended to be implanted. For the exemplary embodiment, the valvular element 120 shown in FIG. 1 includes three leaflets 122 for a tri-leaflet configuration. Other configurations including different numbers of leaflets are, however, also contemplated. For example, mono-leaflet, bi-leaflet and/or multi-leaflet configurations are also possible.

The leaflets 122 and the support 124 may be operably attached to the expandable stent 110 by any means known in the art, such that the leaflets 122 can preferably repeatedly move between an open state and a closed state for unidirectional flow of a liquid (e.g., blood) through a lumen of the prosthetic heart valve 100. In one embodiment, the support 124 of the valvular element 120 may be attached to the expandable stent 110 by suturing. Other means for attachment are, however, contemplated by the invention. As one option, the support 124 may be eliminated from the device 100, and the leaflets 122 may be directly attached to the expandable stent 110.

The valvular element 120 may be attached to the expandable stent 120 at any location along its length, as desired for a particular application. In the device shown in FIG. 1, the valvular element 120 is located at or near the middle of the expandable stent 110 (along its length), but other locations are also possible.

As used herein, an undeployed state of the prosthetic heart valve 100 is the state of the prosthetic heart valve 100 at the time the valve is outside the body and as may be provided on a delivery device (e.g., on a catheter or a sheath), and a deployed state is the state of the prosthetic heart valve 100 at the time the prosthetic heart valve 100 is to be left in the body.

As discussed herein, a prosthetic heart valve implanted to replace, for example, a mitral valve, can be difficult to place properly in a mitral valve annulus. In addition, if improperly positioned or sized, a prosthetic heart valve can move or migrate due to the forces acted upon the valve by surrounding blood. Spring 130 is attached to the first end 112 of the expandable stent 110 thereby to assist in proper placement and to reduce the likelihood that the prosthetic heart valve 100 will migrate after the prosthetic heart valve 100 is delivered and implanted at a delivery site, as well as throughout the life of the prosthetic heart valve 100.

The spring 130, shown in FIGS. 1 and 2, comprises a wire that is wound or coiled such that the spring 130, when expanded, has a generally circular shape. Other numbers of wires and other configurations of the spring 130 are, however, also contemplated by the invention. For example, there may be a different number of times that the spring 130 coils or is wound around a central axis 117. In addition, the distance between individual coils (or times the wire is wound around the central axis) of the spring 130 may be varied. The individual coils or times the spring 130 is wound are shown in FIG. 1 as being in direct or close contact to each other. However, alternative configurations are also contemplated in which more space between the individual coils is found in an expanded configuration of the spring 130 (not shown).

The preferred spring 130 is a torsion spring. While not wishing to be bound by theory, a torsion spring is a spring that works by torsion or twisting; that is, a flexible, elastic object that stores mechanical energy when it is twisted. The amount of force (torque) it exerts is proportional to the amount it is twisted. The spring 130 is able to exert force radially against a body lumen into which it is implanted, in order to hold the prosthetic heart valve 100 in place inside the body lumen.

The spring 130 preferably comprises a shape memory material, as those described above with regard to the expandable stent 110. However, other materials are also contemplated by the invention.

The spring 130 is preferably provided as a coil and is wound and radially compressed when the prosthetic heart valve 100 is undeployed and located within a delivery device (e.g., a sheath or catheter). Winding the spring 130 up allows the diameter of the spring 130 to be reduced in order to fit in a delivery device. When the prosthetic heart valve 100 is deployed, the spring 130 will expand to a predetermined diameter in order to contact tissue, or an inner surface of a body lumen, and hold the device 100 in place. While not wishing to be bound by theory, compressed torsional energy in the undeployed device is used to change the diameter of the spring 130 from a small diameter state (during delivery) to a large delivery state (following delivery). The preferred diameter of the small diameter state is less than about 9.3 mm (28 French) and the preferred diameter of the large delivery state of the spring 130 is about 2 cm to about 5 cm, depending upon the expansion of the expandable stent portion 120 or the valve support 124 or frame. Alternatively, the diameter of the larger delivery state can be determined based upon the diameter of the expandable stent portion in its expanded configuration. Preferably, the larger delivery state of the spring 130 could then have a diameter that is between about 0 cm to about 1 cm larger than the larger delivery state diameter of the expandable stent portion.

The material comprising the spring 130 and the configuration of the spring 130 preferably ensures adequate radial stiffness of the spring 130 for a given application. In the embodiment shown, the spring 130 is configured to ensure that there will be sufficient contact between the prosthetic heart valve 100 and the body lumen (i.e., a sufficient fit) into which the prosthetic heart valve 100 fits (e.g., a mitral valve annulus). The fit minimizes the chance of migration of the prosthetic heart valve 100 as forces are applied to the prosthetic heart valve 100 by surrounding blood. The presence of the spring 130 also may eliminate the need to anchor the device 100 into tissue by using, for example, barbs or hooks. Beneficially, the prosthetic heart valve 100 may be used without penetrating tissue of the heart in order to hold the valve 100 in place.

Figure 21:
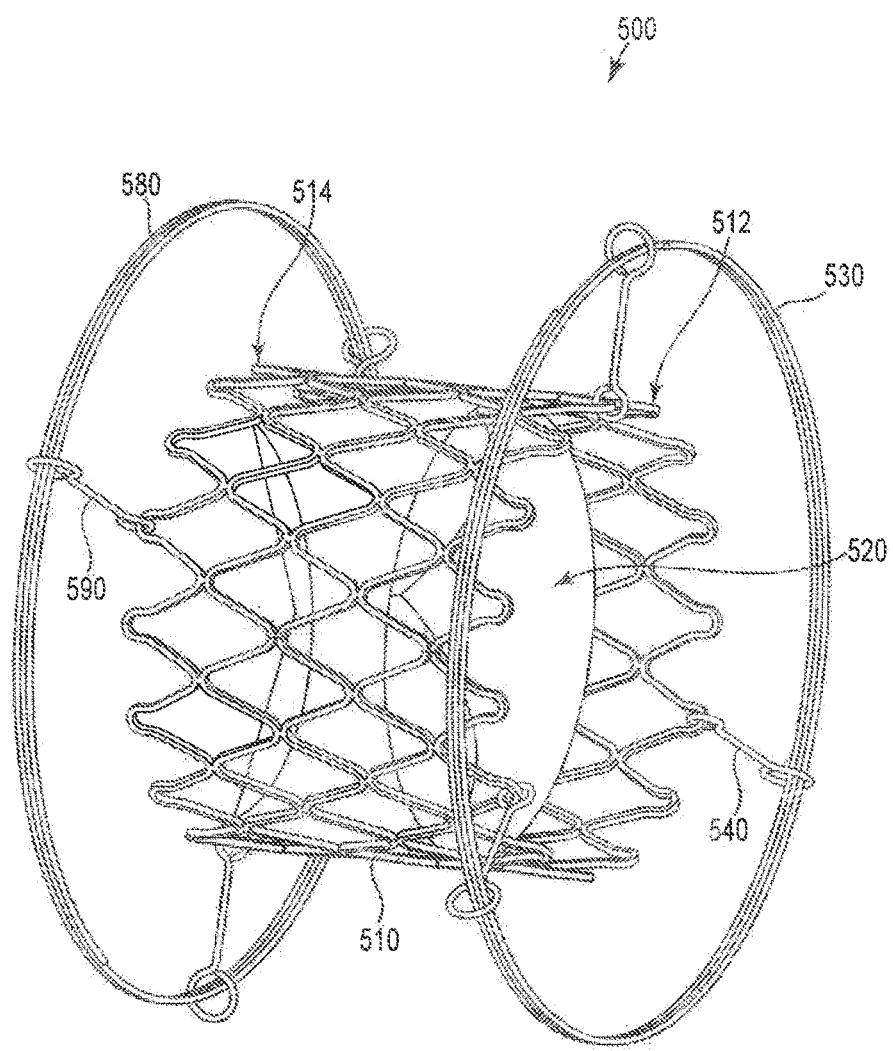
FIG. 21 illustrates a perspective view of an embodiment of a prosthetic valve, of the invention, including two springs.

As an alternative, in another embodiment, there may be springs located on both the first and the second end of the expandable stent. FIG. 21 illustrates this alternative prosthetic heart valve 500. The device 500 preferably includes corresponding features, e.g., expandable stent portion 510 with first end 512 and second end 514, valvular element 520 and first spring 530 with support arms 540. However, a second spring 580 is attached to the second end 514 of the expandable stent portion 510 using support arms 590. The addition of the second spring 580 may provide additional resistance against migration of the prosthetic heart valve 500, or resistance against migration in a different direction from that provided by the first spring 530. Therefore, it is contemplated that the prosthetic heart valve of the invention may include more than one spring.

Depending upon the location of the spring or springs in the prosthetic heart valve of the invention, migration in one or more directions may be prevented. For example, in the embodiment shown in FIGS. 1 and 2, the spring 130 is preferably implanted on the atrial side of the mitral valve annulus, and the remainder of the expandable stent 110 extends through the annulus and into the left ventricle. As a result, the prosthetic heart valve 100, upon implantation, prevents migration of the prosthetic heart valve 100 from the left atrium and into the left ventricle. However, if a second spring would be included and implanted on the ventricular side of the mitral valve annulus, then migration of the prosthetic heart valve from the left ventricle and into the left atrium would also be prevented.

If one spring 130 is used on the prosthetic heart valve 100, as in FIGS. 1 and 2, a flare or anchor (not shown) may be optionally included on the opposite end of the expandable stent portion 110 from the spring 130. The purpose of such flares or such anchors would be to preferably anchor the second end 114 of the expandable stent portion 110 (but also could anchor the first end 112) into tissue opposite (or adjacent) the spring 130. Instead of anchoring into tissue (e.g., by using barbs), it may be possible that the location and design of the anchors would contact the side of the valve annulus opposite the side including the spring 130 without penetrating tissue.

Figure 22:
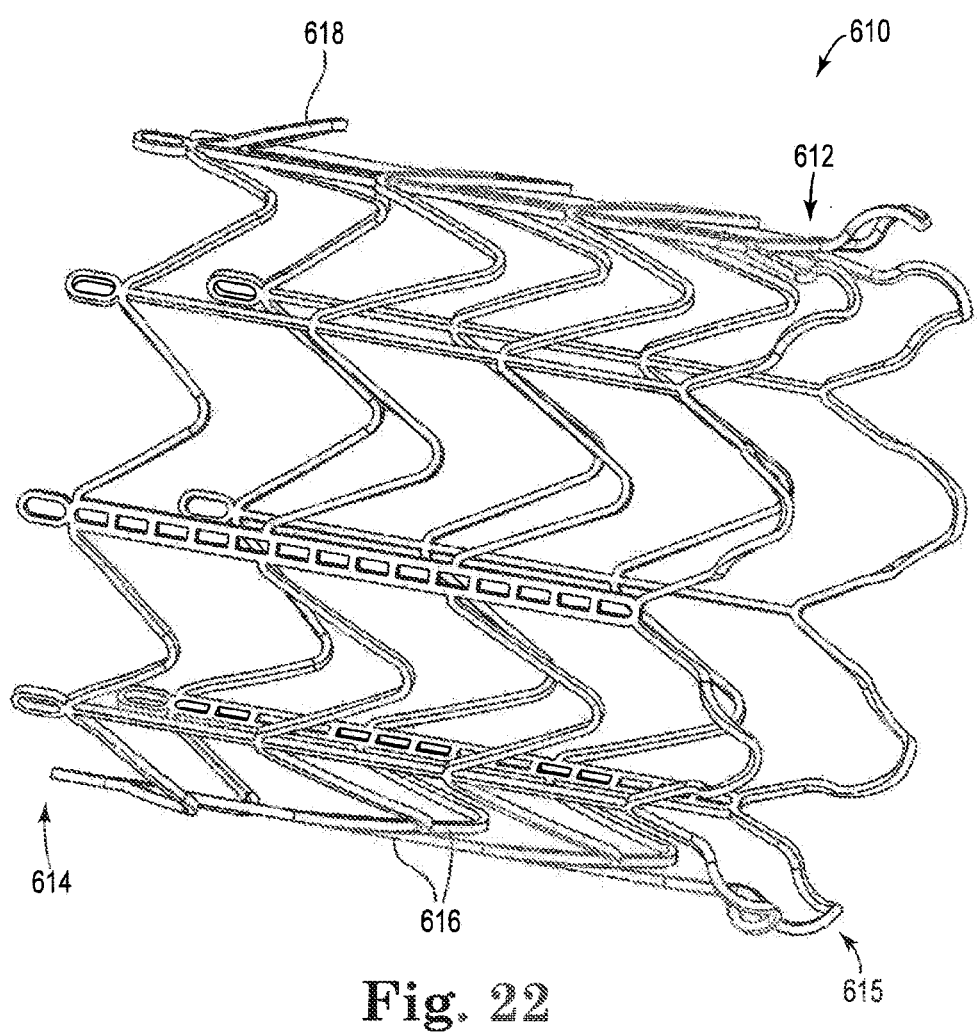
FIG. 22 illustrates a perspective view of an expandable stent portion of an embodiment of a prosthetic valve, in accordance with the invention, including an anchor.

In one example of anchoring the stent, the entire end of the stent could be flared, as shown by 615 in FIG. 22, to a larger diameter. The flare 615 could, however, be on the second end 614 of the stent portion 610 alternatively. Any suitable type of flare, in addition to the flare 620 shown in FIG. 22, is contemplated for use with prosthetic heart valve 100.

One example of a type of anchor that may be used is also illustrated in FIG. 22. FIG. 22 shows an alternative expandable stent portion 610. At or near the second end 614 of the stent portion 610, which will be opposite the first end 612 that is intended to be attached to a spring, one or more anchors 618 will be present. In the embodiment shown, the anchor 618 is actually a flared portion of one of the plurality of wires 616 or members that make up for the expandable stent portion 610. Preferably, there are at least three of these anchors 618 per expandable stent portion 610, but any suitable number is contemplated. The anchor 618 shown in FIG. 22 is, however, only one exemplary anchor. Other anchors are contemplated, which may, for example, include a separate anchoring system that is not part of the stent portion. If the anchoring system is separate, the system may be employed during deployment of the prosthetic heart valve of the invention or may be included post-implant. Some additional examples of such anchors include, but are not limited to, U-clips and sutures.

In the preferred embodiment, shown in FIG. in order to connect the spring 130 to the expandable stent 110, a plurality of support arms 140 are preferably used, although other suitable means for attachment are also contemplated. The support arms 140 are preferably pivotable, rotatable, or otherwise moveable or maneuverable in order to allow the spring 130 and expandable stem 110 to expand to its desired diametric configuration without restriction. The length of the support arms 140 can control the amount of diametric or radial expansion of the spring 130 due to their length, Thus, the length of the support arms 140 will be dependent upon the use of the prosthetic heart valve and desired deployed diameter of the spring 130. Shorter support arms 140 will limit the amount of unwinding of the spring 130 and longer support arms 140 will allow for more expansion of the spring 130. The amount of expansion of the spring 130, therefore, can relate to the length of the supports arms 130 as well as other factors.

As shown in FIG. 1, the support arms 140 are connected at a first end 142 of the support arms 140 to the expandable stent 110 by a loop or eyelet 146 formed by the wire comprising the support arm 140 itself. However, other means for attaching the support arms 140 to the expandable stem 110 are also contemplated. For example, a means for attaching the support arms 140 to the expandable stent 110 that allows the support arms 140 to pivot with respect to the expandable stem 100 is a possible embodiment. Preferably, the support arms 140 are attached to the expandable stent 110 around the circumference of the first end 112 of the expandable stent 110. Preferably, the support arms 140 are generally evenly spaced around the circumference of the first end 112 of the expandable stem 110, however other spacings are also contemplated.

The support arms 140 are attached to the spring 130 at a second end 144 of each support arm. Preferably, and as shown, loops or eyelets 148 are located on the second ends 144 of the support arms 140 through which the spring 130 extends. The spring 130 is preferably able to slide through the loops or eyelets 148 on the support arms 140 in order for the spring 130 to be deployed or expanded. However, other suitable means for attachment to the spring 130 are also contemplated by the invention such that the spring 130 is able to unwind as needed.

The support arms 140 preferably comprise a shape memory material, such as those provided above with regard to the expandable stent 110. A preferred material is Nitinol™. However, other materials are also contemplated by the invention.

Preferably, the stiffness or rigidity of the material used to form the support arms 140 is generally greater than the stiffness or rigidity of the material used to form the spring 130. The relative stiffnesses allows the support arms 140 to maintain a desired expanded diametric configuration of the spring 130 after the device 100 is deployed and undergoes forces within a beating heart, for example. Other relative stiffnesses of the support arms 140 and spring 130, however, are also contemplated by the invention.

The number of support arms 140 may vary, according to the invention. Three support, arms 140 are shown in the figures. However, it is contemplated that other numbers of support arms 140 are possible, such that the support arms 140 are able to sufficiently hold the spring 130 in its desired expanded diametric configuration.

The support arms 140 shown are generally linear in shape. However, other shapes are also contemplated that may control deployment of the spring 130. For example, another possible embodiment of the prosthetic heart valve may include a plurality of support arms that when deployed are curved. For example, a deployed prosthetic heart valve may include a plurality of support arms that are all similarly curved. A potential benefit of using curved support arms is that if they collapse, the arms will collapse radially rather than axially. Other shapes and configurations of the support arms are also contemplated.

The number of loops 148 and location of the loops 148 on the support arms 140 may be varied. For example, additional loops may be found along the length of the support arms 140 (not shown). The spring 130 may also be extended through the additional loops. The addition of more loops may be for the purpose of preventing kinking, tangling or twisting of the spring or to better control expansion of the spring to its desired diametric configuration, for example.

Preferably, when the support arms 140 are fully extended and the spring 130 is released to its desired expanded diameter, the support arms 130 will extend generally or nearly perpendicular to a central, longitudinal axis 117 of the expandable stent 110. In FIGS. 1 and 2, the support arms 140 do not extend exactly perpendicular to central axis 117. It is contemplated that the support arms 140 may extend at various angles with respect to the central, longitudinal axis 117 of the expandable stent 110, as desired for a particular application.

As will be appreciated, the prosthetic heart valve 100 can be treated and/or coated with any number of surface or material treatments. Examples of such treatments include, but are not limited to, bioactive agents, including those that modulate thrombosis, those that encourage cellular in-growth, through-growth, and endothelization, those that resist infection, and those that reduce calcification.

Figure 3:
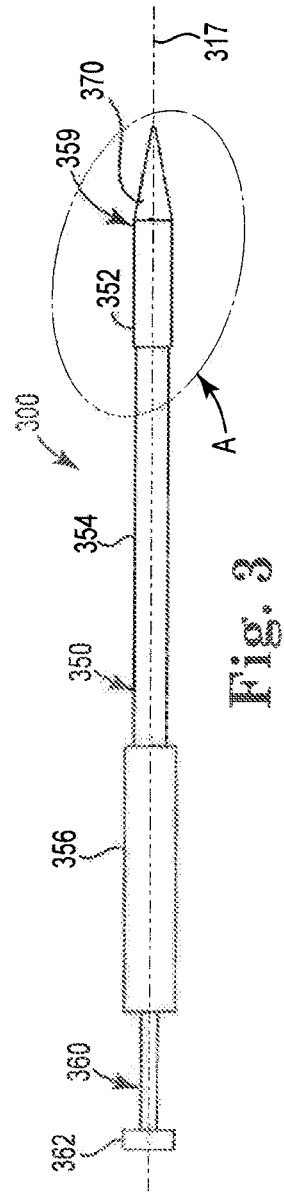
FIG. 3 illustrates a side view of a system, in accordance with the invention.
Figure 4:
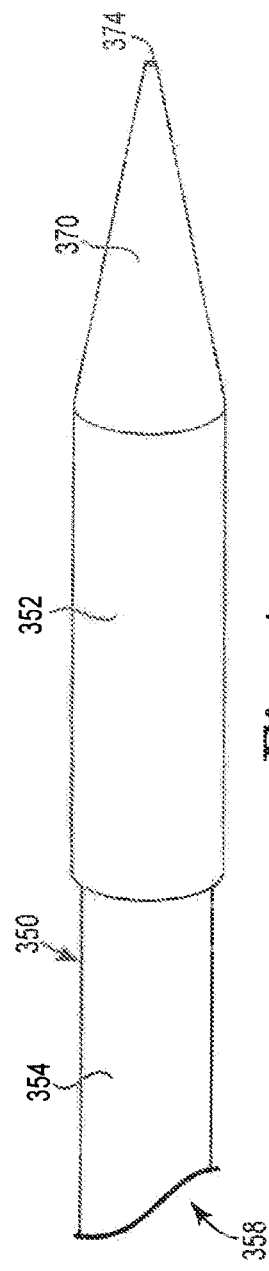
FIG. 4 illustrates a perspective view of distal end portion A of the system shown in FIG. 3.
Figure 5:
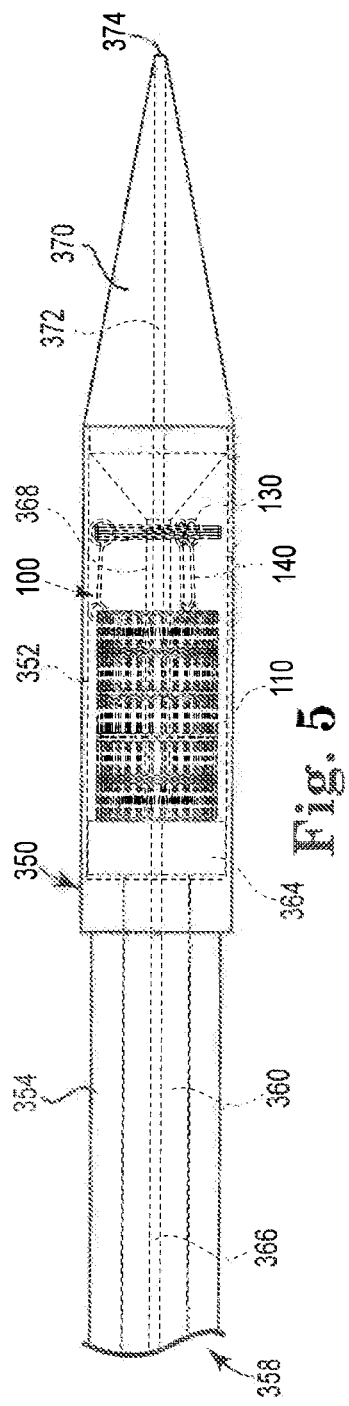
FIG. 5 illustrates a side view of distal end portion A of the system shown in FIG. 3, with interior shown in shadow.

The prosthetic heart valve 100 described above, or other embodiments of the invention, may be a part of a system for replacement of a native valve with a prosthetic heart valve. FIG. 3 illustrates an embodiment of such a system 300 of the invention. The system 300 shown encloses the prosthetic heart valve 100, as described above, or other such prosthetic heart valve in accordance with the invention, in order to deliver the valve to its desired location in a body lumen. The system 300 shown is one embodiment, and other suitable systems are also contemplated. FIGS. 4 and 5 illustrate a distal end portion of system 300, with the distal end indicated in FIG. 3 by the circled portion that is labeled as A. FIG. 4 illustrates a perspective view of distal end A and FIG. 5 illustrates a side view of distal end A, with a collapsed, or non-deployed prosthetic heart valve 100 shown in shadow in the interior of an elongate sheath 350.

System 300 is exemplary, but includes elongate sheath 350 having an inner lumen 358 running along the length of the sheath 350. The sheath 350 is shown as having multiple portions 352, 354, 356 with different diameters. However, it is contemplated that the sheath 350 may have only one diameter, or other numbers of diameters along its length. Preferably, the sheath 350 or portions of the sheath will have a diameter of about five (5) millimeters (mm). Most preferably, the diameter of the sheath 350 is less than about 10 mm (30 French).

In order to deploy the device, preferably the sheath 350 is withdrawn or retracted, which allows the device 100 to expand. As described above, the sheath 350 may have multiple portions, e.g., 352, 354, 356. One alternative embodiment provides for only sheath portion 352 to be withdrawn in order for the device 100 to be deployed. Sheath portion 354 would remain stationary in that embodiment. For example, sheath portion 352 may be withdrawn using actuators that are linear or coaxial on the pushing rod or handle of the system 100.

System 300 also includes a pushing rod 360 that extends into the inner lumen 358 of the sheath 350. The pushing rod 360 has a proximal end 362 that prevents the rod from completely extending into the inner lumen 358. The proximal end also is preferably able to be held by an operator of the system 300. At the opposite end of the pushing rod 360, is a distal end 364. The distal end 364 of the pushing rod 362 is preferably placed against the second end 114 of prosthetic heart valve 100, for example. In order for the prosthetic heart valve 100 to be deployed from sheath 350, the distal end 364 of the pushing rod 360 is held against the device 100, and the sheath 350 is withdrawn or retracted, which results in the device 100 exiting the distal end 359 of sheath 350, and, ultimately, being deployed from the system 300 (as shown in later figures).

The pushing rod 360 also preferably includes an inner lumen 366 (FIG. 5) through which a guide wire or other guiding mechanism for the system 300 may extend. The use of a guide wire (not shown) with the system 300 is preferred, but is not required. The guide wire may also be considered an elongate delivery catheter.

The system 300 also preferably includes a dilator 370 on or near the distal end 359 of sheath 350. The dilator 370 is used to dilate a body lumen or tissue through which the system 300 is desired to extend or penetrate. The dilator 370 is not required, however, and the system 300 may not include one. The preferred dilator 370, however, includes an inner lumen 372 such that the optional guide wire discussed above may also extend through dilator 370 and out an end opening 374 of the dilator 370. If the dilator 370 is included, the pushing rod 360 preferably will include an extension 368 having a preferably narrower diameter that connects the pushing rod 360 to the dilator 370, or the dilator may be otherwise attached to the pushing rod 360. Preferably, the dilator 370 remains stationary with the pushing rod 360 while the sheath 350 is withdrawn or retracted, allowing the device 100 to exit the sheath 350. In another alternative embodiment, a dilator could actuate independent from the remainder of the delivery system.

FIG. 5 shows, in shadow, how the prosthetic heart valve 100 preferably looks prior to deployment. The prosthetic heart valve 100 is shown in a folded, collapsed or undeployed position and inserted into sheath 350 for delivery to an implantation position in a body lumen or annulus. The sheath 350 is positioned to releasably hold the prosthetic heart valve 100 in a delivery, or undeployed, state. The spring 130 is shown more tightly coiled than when deployed. The support arms 140 are extending generally parallel to a central axis 317 of the system 300. The prosthetic heart valve 100 is preferably loaded in the system 300 such that the extension 368 of the pushing rod 360 extends through the inner lumen 119 of the prosthetic heart valve 100, as shown.

The length of pushing rod 360 is shown for purposes of illustration only. Depending upon the application of the system 300, the length of the pushing rod 360 and sheath 350 may be varied. The invention contemplates other lengths.

The system 300 shown in FIG. 3 is one embodiment of the inventive system. Rather than a pushing rod and sheath configuration, it is contemplated that other means for deploying a prosthetic heart valve of the invention are possible. For example, a retractable sheath surrounding the prosthetic heart valve 100 may be used instead. Any suitable means for delivery of the prosthetic heart valve 100 is contemplated.

The sheath 350 can include an inner lining (not shown) on an inner surface of the sheath 350. An inner lining can decrease friction between the prosthetic heart valve device 100 and the sheath 350 while also sealing the sheath 350. The inner lining can be formed of, for example, nylon, Dacron™, expanded polytetrafluoroethylene (ePTFE), and/or other materials.

The sheath 350 can have many possible configurations. For example, in some embodiments, the sheath 350 can be a flexible tube formed of a metal, metal-alloy, and/or polymers, such as polyvinyl chloride, polyethylene, polyethylene terephalate, polyimide, mixtures, and block-copolymers thereof.

The pushing rod 360 and dilator 370 may be formed, for example, by similar materials to those used for the sheath 350. The guide wire may be made of conventional materials. The invention does, however, contemplate that any suitable materials may be used for the components of the system 300.

The valve replacement system 300 will be used in a description below of an inventive method for replacement of a heart valve. Specifically, the method described may be used to deliver prosthetic heart valve 100 to a mitral valve, for example. However, it will be understood from the following description that the invention could be used instead to replace any heart valve or other suitable valve in a body lumen or valve annulus.

To implant the prosthetic heart valve 100, for example, the prosthetic heart valve 100, as described above, is compressed into its collapsed position and inserted into the sheath 350 that has a suitably sized lumen for accepting the compressed prosthetic heart valve 100 (as shown in FIG. 5). The system 300 may be supplied with the prosthetic heart valve 100, for example, already loaded, or instead may require that an operator load the device.

The sheath 350, including the prosthetic heart valve 100, is then guided in the conventional fashion (with or without the use of a guide wire) or advanced to a position adjacent an implantation position in a patient's heart (for example, adjacent the mitral valve annulus). The sheath 350 is preferably delivered to or deployed at a pre-selected position in an anatomical lumen of the heart. The pre-selected position may be, for instance, in proximity to the original location of a natural heart valve.

One preferred method of delivering a prosthetic heart valve to a body lumen includes introducing a mitral valve prosthetic heart valve device, such as prosthetic heart valve 100, to the mitral valve annulus using minimally invasive techniques. Preferably, the heart is off-pump. Preferably, a lower mini-sternotomy or thoracotomy is performed and a standard transapical approach is used for placement of a mitral valve prosthetic heart valve device. However, other anatomical approaches and surgical methods are contemplated for the inventive system 300.

Figure 18:
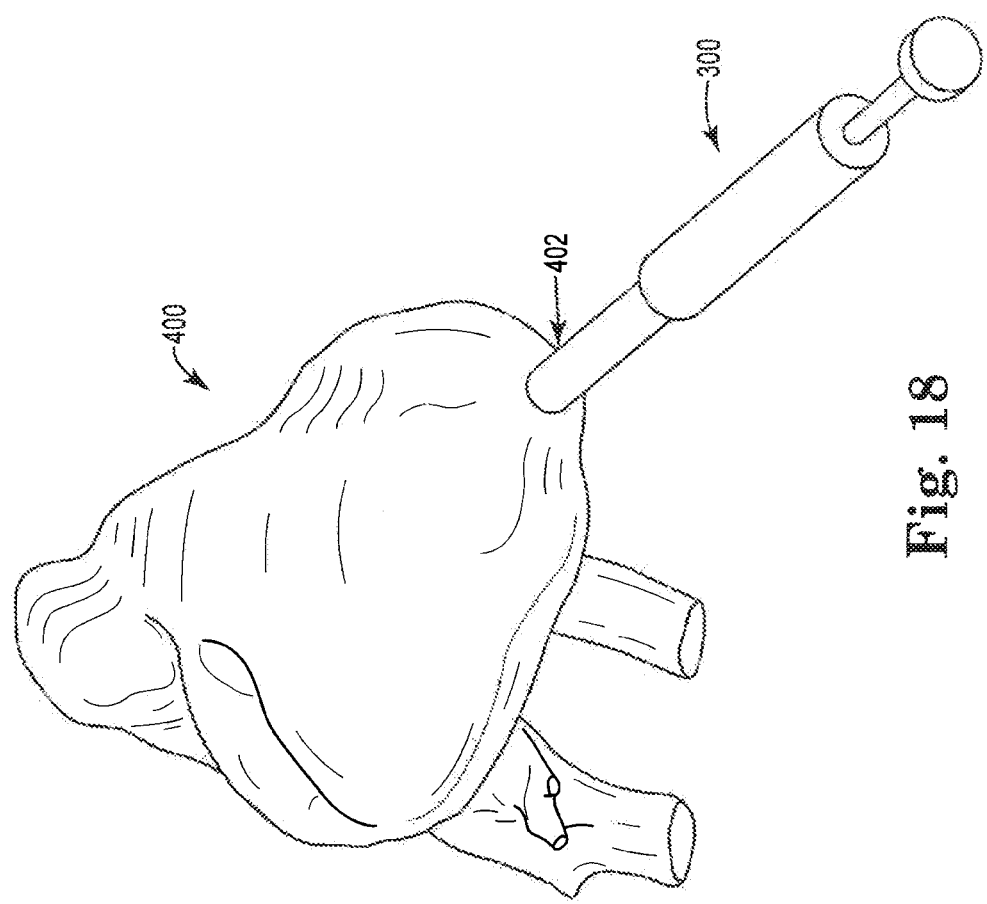
FIG. 18 illustrates a heart with the inventive system being inserted into the apex of the heart.

FIG. 18 shows the system 300 inserted into a heart 400 via a transapical approach. In the figure, the system 300 is partially inserted into an opening 402 made in the apex of the heart 400. The opening 402 is made by puncturing the apex of the heart with the distal end of system 300 or using another instrument prior to introduction of the system 300.

The initial step of inserting or introducing and advancing the system 300 to a desired location, such as into the apex of the heart, as described above, may preferably be done using the aid of a fluoroscope or some other image guidance, in order to view the placement within the body. Imaging devices (not shown) may be used to permit the surgeon (operator) to watch and guide the movement of the prosthetic heart valve device to the implantation position. Some possible image guidance include, but are not limited to, fluoroscopy, ultrasonic means, magnetic resonance, X-ray, computer tomography, and combinations thereof.

Preferably, the prosthetic heart valve 100 includes materials that are radiopaque so that the device can be viewed using imaging devices. For example, a plurality of radiopaque markets may be disposed on the stent and/or coil portions of the device. Radiopaque markets may include radiopaque metals such as, for example, gold and platinum. Examples of suitable radiopaque that may be added to polymeric materials in the device include, but are not limited to, barium sulfate and bismuth sub-carbonate.

Next, once the system 300 is in its desired location in the body, the pushing rod 360 is pushed in a distal direction. FIG. 6 shows the system 300 as the prosthetic heart valve 100 is just beginning to be deployed from the distal end 359 of sheath 350. As illustrated, the spring 130 and support arms 140 have exited the sheath 350 and the spring 130 appears in its desired partially expanded configuration. The support arms 140 are generally perpendicular to a central, longitudinal axis 317 extending though the system 300. The expandable stent 110 of the prosthetic heart valve 100 has not yet completely exited the sheath 450.

FIGS. 7 and 8 illustrate a distal end portion (indicated as B) of system 300, at the stage of deployment as in FIG. 6. FIG. 7 illustrates a perspective view of distal end B and FIG. 8 illustrates a side view of distal end B.

FIG. 9 illustrates the system 300 after the pushing rod has been pushed even further distally than in FIG. 6. As shown, the expandable stent portion 110 has partially exited the distal end 359 of the sheath 350.

FIGS. 10 and 11 illustrate a distal end portion (indicated as C) of system 300, at the stage of deployment as in FIG. 9. FIG. 10 illustrates a perspective view of distal end C and FIG. 11 illustrates a side view of distal end C. FIG. 11 also shows, in shadow, the remainder of the prosthetic heart valve 100 that has not yet exited the sheath 350, as well as the pushing rod 360.

At this point in the delivery of the prosthetic heart valve 100, it is preferred for the surgeon (or operator) to pull the whole system 300, including the prosthetic heart valve 100, back proximally. The proximal pull preferably enables the spring 130 to engage into the proper implantation position. For the mitral valve, for example, the system 300 is pulled back once the device 100 has partially exited sheath 350, with sheath 350 being in the vicinity of the mitral valve annulus. Preferably, in the mitral valve application, the spring 130 is seated in the left atrium adjacent the atrial side of the mitral valve annulus. Depending upon the desired location and purpose for the prosthetic heart valve, however, adjustments may be made in order to allow for proper placement of the prosthetic heart valve.

Although the embodiment of the inventive system shown and described herein may not allow the prosthetic heart valve 100 to be retracted back into the sheath 350 for possible re-positioning, it is contemplated that other embodiments of inventive systems may have such an ability. For example, the prosthetic heart valve may be configured such that the expandable stent, support arms and spring may be retracted back into the sheath after being either partially deployed or completely deployed. Retractability may be desired, for example, if during deployment the surgeon (or operator) recognizes by image guidance means that the prosthetic heart valve is not being deployed in a proper place.

FIG. 12 illustrates the system 300 once the pushing rod 360 has been pushed even further distally from the stage of deployment shown in FIG. 9. Prosthetic heart valve 100 is no longer enclosed in the sheath 350, and is fully deployed.

FIGS. 13 and 14 illustrate a distal end portion (indicated as D) of system 300, at the stage of deployment as in FIG. 12. FIG. 13 illustrates a perspective view of distal end D and FIG. 14 illustrates a side view of distal end D.

Figure 15:
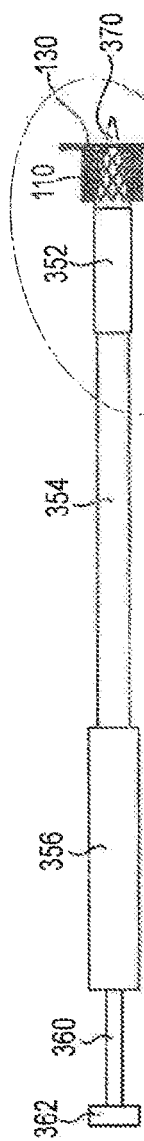
FIG. 15 illustrates a side view of the system of FIGS. 3, 6, 9, and 12 at a later stage in delivery of the prosthetic heart valve of the system.

FIG. 15 illustrates the system 300 once the prosthetic heart valve 100 has been fully deployed. The pushing rod 360 has been pulled proximally in order to pull the dilator 370 back in contact with the sheath 350. Next, the sheath 350, pushing rod 360 and dilator 370 will be retracted and removed from the body, leaving the prosthetic heart valve 100 behind.

Figure 16:
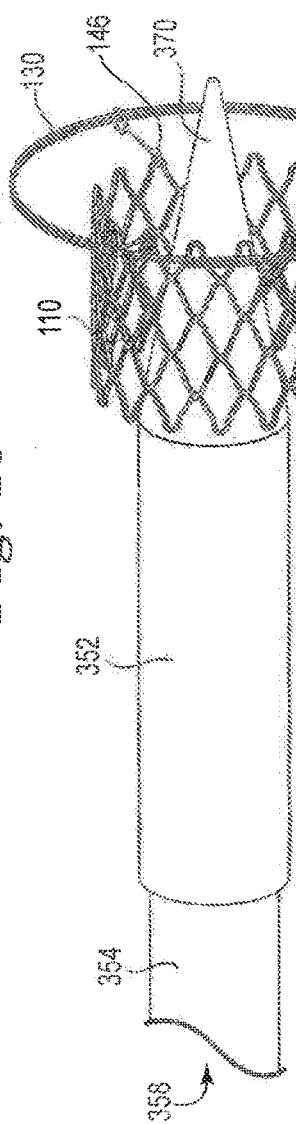
FIG. 16 illustrates a perspective view of distal end portion E of the system shown in FIG. 15.
Figure 17:
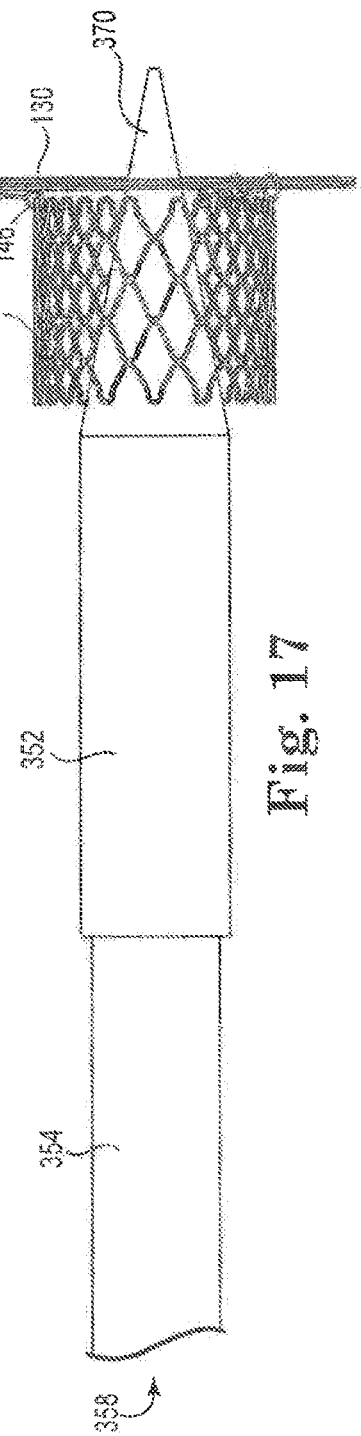
FIG. 17 illustrates a side view of distal end portion E of the system shown in FIG. 15.

FIGS. 16 and 17 illustrate a distal end portion (indicated as E) of system 300, at the stage of deployment as in FIG. 15. FIG. 16 illustrates a perspective view of distal end E and FIG. 17 illustrates a side view of distal end E.

Figure 19:
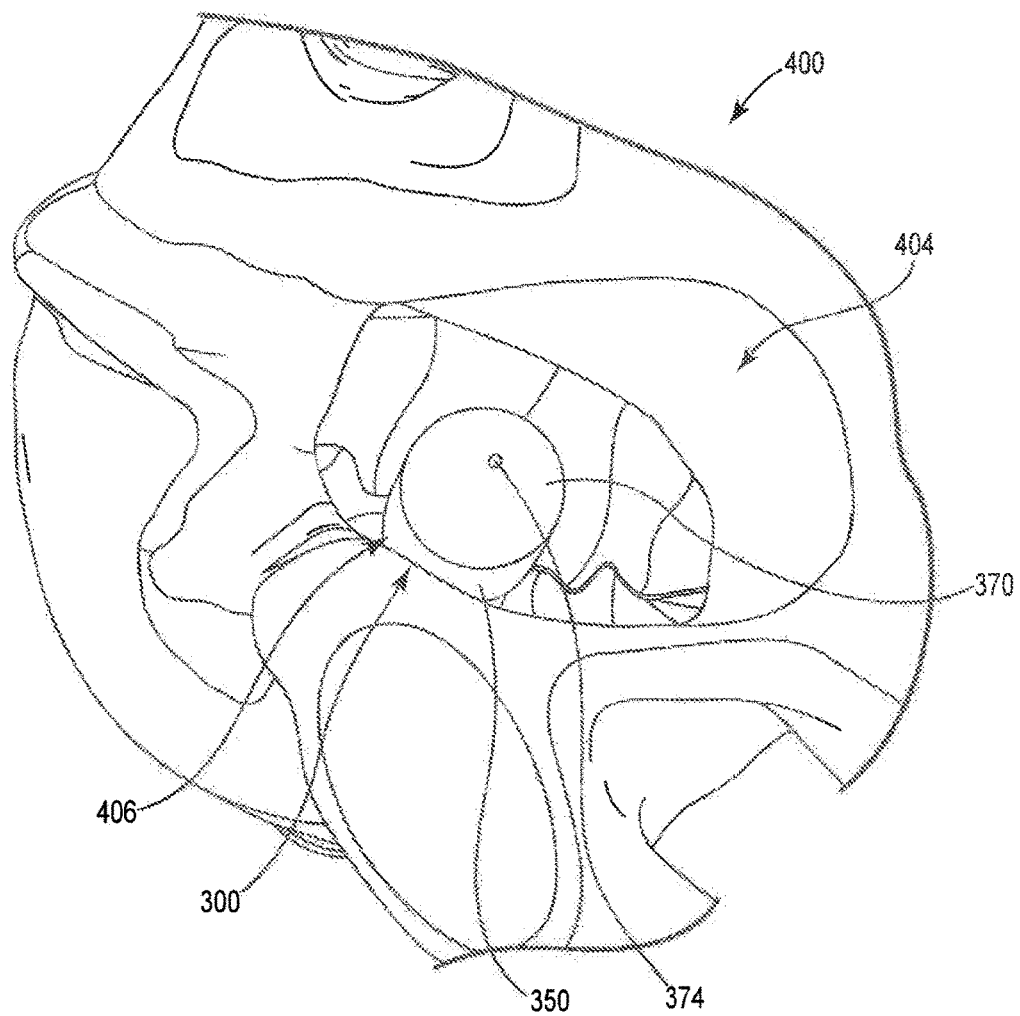
FIG. 19 schematically illustrates a top view of a heart with left atrium partially cut-away in order to view the inventive system being inserted through a mitral valve annulus.
Figure 20:
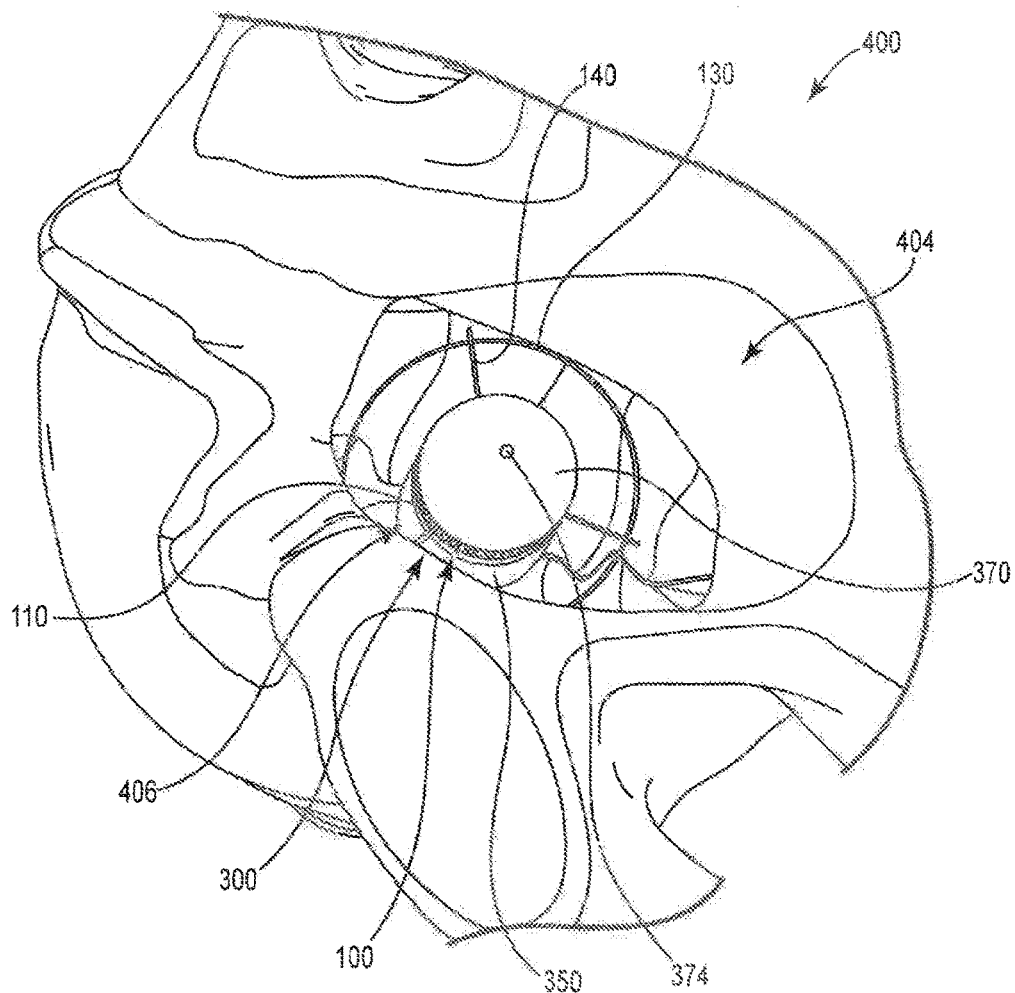
FIG. 20 is the heart and system shown in FIG. 19 with the prosthetic valve device of the system being partially deployed.

FIGS. 19 and 20 are schematic representations of a heart 400 with a view from above and including a view into a left atrium 404 (some of left atrium is cut-away in figure). FIG. 19 shows the inventive system 300 inserted through the Initial valve annulus 406, with its distal end, including dilator 370 (with opening 374) and sheath 350, extending into the left atrium 404. FIG. 20 shows the inventive prosthetic valve 100 partially deployed, with the amount of deployment being approximately as in the system 300 shown in FIGS. 6-8. As shown, expandable stent portion 110 has partially exited or been partially deployed from the distal end of sheath 350. Three support arms 140 are extended and spring 130 is released or deployed, and is being held through loops (not visible) on ends of the support arms 140.

In an alternative embodiment of the system of the invention, it may be desired to includes means for keeping the expandable stent portion inside a retractable sheath and compressed until the retractable sheath has been retracted enough to fully clear the expandable stent portion. Therefore, the expandable stent portion would not be in a partially deployed configuration as in earlier figures. This alternative embodiment may be desired because it is possible that stored energy in a compressed end of the prosthetic heart valve may force the expandable stent portion out of a distal end of a sheath prematurely and before the expandable stent portion is desired to be fully deployed. Such premature release of the prosthetic heart valve could result in improper placement of the device, for example. In order to avoid such premature release upon deployment, the invention contemplates using means to prevent such premature release.

Figure 23:
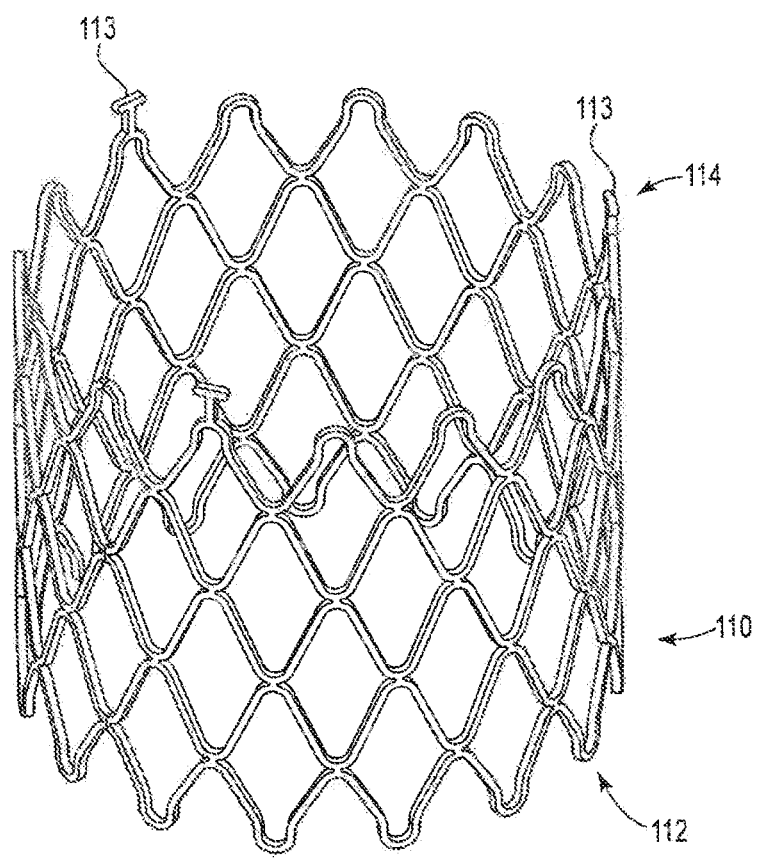
FIG. 23 illustrates a perspective view of an expandable stent portion of an embodiment of a prosthetic valve, in accordance with the invention.
Figure 24:
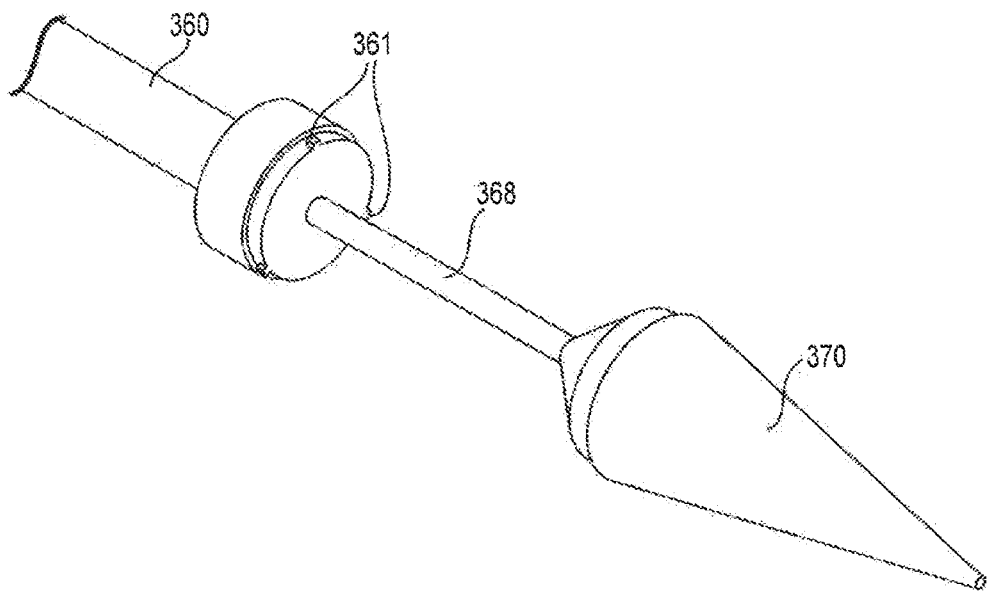
FIG. 24 illustrates a perspective view of a distal end portion of an embodiment of a system, in accordance with the invention.

FIGS. 23 and 24 show illustrative means for preventing premature release of the device from a delivery system. For example, in FIG. 23, retainers 113 are added to the second end 114 of the expandable stent portion 110 that prevent the expandable stent portion 110 from exiting the sheath 350 until the expandable stent portion 110 has fully cleared the sheath 350. The retainers 113 would mate, for example, with some portion of the pushing rod 360. In FIG. 24, another alternative means for preventing premature release of the device from the delivery system 300 is shown as bosses 361 located on the pushing rod 360. the prosthetic heart valve would be enclosed in a retractable sheath (not shown) and surrounding extension 368 of pushing rod 360. The bosses 361 would hold a proximal end of a collapsed prosthetic heart device between the retractable sheath and pushing rod 360 until a proximal end of an expandable sheath portion of the prosthetic heart valve fully cleared the retractable sheath. The bosses 361 and retainers 113 are examples of means for preventing premature release, however, and other means are also contemplated.

All publications, patents and patent documents cited are fully incorporated by reference herein, as though individually incorporated by reference. Numerous characteristics and advantages of the invention meant to be described by this document have been set forth in the foregoing description. It is to be understood, however, that while particular forms or embodiments of the invention have been illustrated, various modifications, including modifications to shape, and arrangement of parts, and the like, can be made without departing from the spirit and scope of the invention.

The invention claimed is:

1. A prosthetic valve, comprising:
   an expandable stent defining a first end, a second end, and an inner lumen, and having a longitudinal axis;
   a valvular element disposed in the inner lumen of the expandable stent;
   an expandable positioning element connected to the first end of the expandable stent wherein the expandable positioning element comprises a wire that forms a circular loop about the longitudinal axis of the expandable stent to be concentric therewith,
   wherein the circumference of the wire loop of the expandable positioning element is greater than a circumference of the expandable stent when the prosthetic valve is in an expanded configuration; and
   a connecting element pivotally attached to the first end of the expandable stent, the connecting element being a separate element from each of the expandable stent and the expandable positioning element, the connecting element also attached, by a loop of the connecting element, to the expandable positioning element such that the expandable positioning element is configured to laterally rotate outward from the first end of the expandable stent during expansion of the expandable positioning element, wherein the connecting element is capable of extending generally perpendicular to the longitudinal axis of the expandable stent when the expandable positioning element is in an expanded configuration, and wherein the expandable positioning element is configured to assist in the proper placement of the prosthetic valve within a body.

2. The prosthetic valve of claim 1, wherein the valvular element comprises at least one leaflet.

3. The prosthetic valve of claim 1, wherein the second end of the expandable stent is flared outward relative to the longitudinal axis of the expandable stent.

4. The prosthetic valve of claim 1, wherein the expandable positioning element comprises a shape memory alloy.

5. The prosthetic valve of claim 1, wherein the expandable positioning element comprises a torsion spring.

6. The prosthetic valve of claim 1, wherein the prosthetic valve is a prosthetic heart valve.

7. The prosthetic valve of claim 6, wherein the prosthetic heart valve is a prosthetic mitral valve.

8. The prosthetic valve of claim 6, wherein the prosthetic heart valve is a prosthetic aortic valve.

9. A prosthetic valve comprising:
   an expandable stent defining a first end, a second end, and an inner lumen, and having a longitudinal axis;
   an expandable spring connected to the first end of the expandable stent wherein the expandable spring is formed from a coil that is wound about the longitudinal axis of the expandable stent to be concentric therewith, wherein the circumference of the coil of the expandable spring is greater than a circumference of the expandable stent when the prosthetic valve is in an expanded configuration; and
   a plurality of support arms connecting the expandable spring to the first end of the expandable stent, wherein each of the plurality of support arms is capable of extending generally perpendicular to the longitudinal axis of the expandable stent when the expandable spring is in an expanded configuration.

10. The prosthetic valve of claim 9, wherein the expandable spring is circular.

11. The prosthetic valve of claim 9, wherein the coil is a plurality of coils and wherein each coil of the plurality of coils is wound about the longitudinal axis of the expandable stent to be concentric therewith.

12. The prosthetic valve of claim 11, wherein the coils contact each other.

13. The prosthetic valve of claim 11, wherein the coils are spaced from each other.

14. The prosthetic valve of claim 9, further comprising a second expandable spring connected to the second end of the expandable stent.

15. A method of implanting a prosthetic valve, comprising:
   inserting a delivery system with a prosthetic valve into a body lumen, the prosthetic valve comprising
   an expandable stent having a first end, a second end, an inner lumen, and a longitudinal axis,
   a valvular element disposed in the inner lumen of the expandable stent; and
   an expandable annular member pivotally connected by a connecting element to the first end of the expandable stent, the connecting element being a separate element from each of the expandable stent and the expandable annular member and having a loop for pivotally connecting with the expandable annular member, wherein the circumference of the expandable annular member is greater than a circumference of the expandable stent when the prosthetic valve is in an expanded configuration;

at least partially deploying the prosthetic valve at an implantation location such that the expandable annular member pivots outwardly relative to the expandable stent to permit expansion of the expandable annular member, wherein the connecting element is capable of extending generally perpendicular to the longitudinal axis of the expandable stent when the expandable annular member is in an expanded configuration; and proximally pulling the prosthetic valve to engage the expandable annular member with a wall of the body lumen.

16. The method of claim 15, wherein inserting the delivery system into the body lumen comprises transapically inserting the delivery system into a heart.

17. The method of claim 15, wherein proximally pulling the prosthetic valve engages the expandable annular member with a heart wall in a left atrium adjacent a mitral valve annulus.

18. The method of claim 15, wherein the expandable annular member comprises a wire.

19. The method of claim 15, wherein the expandable annular member comprises a radiopaque material.

20. The method of claim 15, wherein the step of at least partially deploying the prosthetic valve includes viewing the prosthetic valve using image guidance.

21. The method of claim 20, wherein image guidance may be selected from the group consisting of fluoroscopy, ultrasonic means, magnetic resonance, X-ray, and computer tomography.

22. A method of implanting a prosthetic valve, comprising:

inserting a delivery system with a prosthetic valve into a body lumen, the prosthetic valve comprising a first expandable annular portion having a first end, a second end, an inner lumen, and a longitudinal axis, a valvular element disposed in the inner lumen of the first expandable annular portion, and a second expandable annular portion pivotally connected by a connecting element to the first end of the first expandable annular portion, the connecting element being a separate element from each of the first expandable annular portion and the second expandable annular portion and having a loop for pivotally connecting with the second expandable annular portion, wherein the circumference of the second expandable annular portion is greater than a circumference of the first expandable annular portion when the prosthetic valve is in an expanded configuration;

at least partially deploying the prosthetic valve at an implantation location such that the second expandable annular portion pivots outwardly relative to the first expandable annular portion to permit expansion of the second expandable annular portion, wherein the connecting element is capable of extending generally perpendicular to the longitudinal axis of the first expandable annular portion when the second expandable annular member is in the expanded configuration;

proximally pulling the prosthetic valve to engage the second expandable annular portion with a heart wall in a left atrium adjacent a mitral valve annulus; and fully deploying the prosthetic valve to engage the first expandable annular portion with the mitral valve annulus.

* * * * *